US007560613B2

(12) United States Patent
Caimi et al.

(10) Patent No.: US 7,560,613 B2
(45) Date of Patent: Jul. 14, 2009

(54) PLANT GENE ENCODING TREHALOSE METABOLISM ENZYMES

(75) Inventors: Perry G. Caimi, Kennett Square, PA (US); Saverio Carl Falco, Wilmington, DE (US); Zude Weng, Vernon Hills, IL (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/726,306

(22) Filed: Mar. 21, 2007

(65) Prior Publication Data

US 2008/0009066 A1 Jan. 10, 2008

Related U.S. Application Data

(60) Division of application No. 10/365,970, filed on Feb. 13, 2003, now Pat. No. 7,214,858, which is a continuation-in-part of application No. 09/538,365, filed on Mar. 29, 2000, now abandoned.

(60) Provisional application No. 60/127,187, filed on Mar. 31, 1999.

(51) Int. Cl.
*A01H 5/00* (2006.01)
*A01H 5/10* (2006.01)
*C12N 15/54* (2006.01)
*C12N 15/63* (2006.01)
*C12N 1/00* (2006.01)
*C12P 21/04* (2006.01)

(52) U.S. Cl. .................... 800/298; 800/284; 435/320.1; 435/440; 435/70.1; 536/23.2; 424/93.2

(58) Field of Classification Search ...................... None
See application file for complete search history.

(56) References Cited

U.S. PATENT DOCUMENTS 6,686,516 B2   2/2004   Lebel et al.

FOREIGN PATENT DOCUMENTS

EP         1 002 867 A1    5/2000

OTHER PUBLICATIONS

Vogel, G. et al., Accession No. AF007778, Mar. 9, 1998.*
Romero, C. et al., "Expression of the yeast trehalose-6-phosphate synthase gene in transgenic tobacco plants: pleiotropic phenotypes include drought tolerance." 1997, Planta, vol. 201, pp. 293-297.*
Lazar, E. et al., "Transforming Growth Factor a: Mutation of Aspartic Acid 47 and Leucine 48 Results in Different Biological Activities." 1988, Molecular and Cellular Biology, vol. 8, pp. 1247-1252.*
Broun, P. et al., "Catalytic Plasticity of Fatty Acid Modification Enzymes Underlying Chemical Diversity of Plant Lipids." 1998, Science, vol. 282, pp. 1315-1317.*
Hill, M. A. and Preiss, J. ,"Functional Analysis of Conserved Histidines in ADP-Glucose Pyrophosphorylase from *Escherichia coli*." 1998, Biochemical and Biophysical Research Communications, vol. 244, pp. 573-577.*
Bowie, J. U. et al., "Deciphering the Message in Protein Sequences: Tolerance to Amino Acid Substitutions." 1990, Science, vol. 247, pp. 1306-1310.*
Guo et al, 2004, Proc. Natl. Acad. Sci. USA 101: 9205-9210.*
Schluepmann et al, 2004, Plant Physiol. 135:879-890.*
George F. Kalf et al., The purification and properties of trehalase, J. Biol. Chem. 230;691-698, 1958.
National Center for Biotechnology Information General Identifier No. 2944178, Accession No. AAC39369, Mar. 9, 1998, G. Vogel et al., Trehalose-6-phosphate phosphatases from *Arabidopsis thaliana*: Identification by functional complementation of the yeast tps2 mutant.
National Center for Biotechnology Information General Identifier No. 2944180, Accession No. AAC39370, Mar. 9, 1998, G. Vogel et al., Trehalose-6-phosphate phosphatases from *Arabidopsis thaliana*: identification by functional complementation of the yeast tps2 mutant.
National Center for Biotechnology Information General Identifier No. 4559292, Accession No. AAD22970, Apr. 4, 1999, R. A. Aeschbacher et al., Purification of the trehelase GMTRE1 from soybean nodules and cloning of its cDNA. GMTRE1 is expressed at a low level in multiple tissues.
National Center for Biotechnology Information General Identifier No. 3929389, Accession No. O42783, Jun. 15, 2002, C. D'Enfert et al., Neutral trehalases catalyse intracellular trehalose breakdown in the filamentous fungi *Aspergillus nidulans* and *Neurospora crassa*.
Christophe D'Enfert et al., Mol. Microbiol., 32(3):471-483, 1999, Neutral trehalases catalyse intracellular trehalose breakdown in the filamentous fungi *Aspergillus nidulans* and *Neurospora crassa*.
National Center for Biotechnology Information General Identifier No. 6553894, Accession No. AAF16560, Oct. 12, 2000, X. Lin et al., *Arabidopsis thaliana* chromosome 1 BAC T23K23 genomic sequence.
National Center for Biotechnology Information General Identifier No. 730984, Accession No. P40367, Nov. 1, 1997, M.A. Blazquez et al., Trehalaose-6-P synthase is dispensable for growth on glucose but not for spore germination in *Schizosaccharomyces pombe*.
National Center for Biotechnology Information General Identifier No. 6587856, Accession No. AAF18542, Oct. 12, 2000, X. Lin et al., *Arabidopsis thaliana* chromosome 1 BAC T11/11 genomic sequence.
Miguel A. Blazquez et al., Plant J., 13(5):685-689, 1996, Isolation and molecular characterization of the *Arabidopsis* TPS1 gene, encoding trehalose-6-phosphate synthase.

(Continued)

*Primary Examiner*—Anne R Kubelik

(57) ABSTRACT

This invention relates to isolated nucleic acid fragments encoding trehalose metabolism enzymes, more specifically, alpha, alpha-trehalase, alpha, alpha-trehalose-phosphate synthase or trehalose-6-phosphate phosphatase. The invention also relates to the construction of a recombinant DNA construct encoding all or a portion of the alpha, alpha-trehalase, alpha, alpha-trehalose-phosphate synthase or trehalose-6-phosphate phosphatase, in sense or antisense orientation, wherein expression of the recombinant DNA construct results in production of altered levels of the alpha, alpha-trehalase, alpha, alpha-trehalose-phosphate synthase or trehalose-6-phosphate phosphatase in a transformed host cell.

12 Claims, 3 Drawing Sheets

OTHER PUBLICATIONS

Guido Vogel et al., Plant J., 13(5):673-685, 1998, Trehalose-6-phosphate phosphatases from *Arabidopsis thaliana*: identification by functional complementation of the yeast tps2 mutant.

Karin Lippert et al., Enzyme stabilization of ectoine-type compatible solutes: protection against heating, freezing and drying, Appl. Microbiol. Biotechnol.. 37:61-65, 1992.

Hans J. Bohnert et al., Adaptations to Environmental Stresses, Plant Cell, 7:1099-1111, 1995.

Roger A. Aeschbacher et al., Purification of the trehalase GMTRE1 from soybean nodules and cloning of its cDNA, GMTRE1 is expressed at a low level in multiple tissues, Plant Physiol., 119:489-495, 1999.

Miguel A. Blazquez et al., Trehalaose-6-P synthase is dispensable for growth on glucose but not for spore germination in *Schizosaccharomyces pombe*, J. Bacteriol,, 176(13):3895-3902, 1994.

Salminen et al., Plant Physiol, Enzymes of α,α-Trehalose Metabolism in Soybean Nodules, vol. 81, pp. 538-541, 1986.

* cited by examiner

```
                                                                                 *
SEQ ID NO:16     1  MDMGSGS-SPVITDPISISPPLLGGLTSNLMP-FSVMSGGCSS-SPS--MSAS--SRRK-
SEQ ID NO:20     1  MDLKP-NLNPVLTDATPLTRSRLG-VPSGLSP-YSPIGAT-FP-HGN--MLAI--PRKKT
SEQ ID NO:22     1  L-----VELAMSISN-------TSALPRATVPGIMALLGGVLGLPQKKLLMKTLEDGSVN
SEQ ID NO:24     1  ------------------------------------------------------------
SEQ ID NO:37     1  MDMKSGHSSPVMTDSPPISNSRLT-IRQNRLP-YSSAAATAIS-QNNNLLLTV--PRKKT
SEQ ID NO:38     1  M-----TNQNVIVSDRKPILGLKTITVSVSNSPLFSNSFPTYFNFPRRKLL-KLLEAADKN
                    1                                                             60

*    *  ***              *       ****    *
SEQ ID NO:16    53  --IEEVLVNGLLDAMKSSSPRKKHNLAFGQDNSPEDEPAYTAWLS-KCPSALASFKQIVA
SEQ ID NO:20    52  GILDDFRSSGWLDAMKSSSPTHTKVSKDVSHGIGSPDSAYSTWL-LKFPSALASFDQITN
SEQ ID NO:22    49  K-GGTKVINTWIDSMRASSPTRVKSTQ-----NQDPTS---PWT-LYHPSALSMFDQIVC
SEQ ID NO:24     1  ------------------------------------------------------------
SEQ ID NO:37    56  GILDDVKSNGWLDAMKSSSPPPTILNKD-NLSNDATDMTYREWMQLKYPSALTSFEKIMS
SEQ ID NO:38    56  NLVVAPKITSMIDSMRDSSPTRLRSSSYDSDSDNDDKT---SWI-VRFPSALNMFDEIVN
                    61                                                            120

*  **************   *  *  ** *  **       **   ** ***   *
SEQ ID NO:16   110  NAQGRRIAVFLDYDGTLSPIVDDPDKAFMSPVMRAAVRNVAKYFPTAIVSGRSRKKVFEF
SEQ ID NO:20   111  CAKGKRIALFLDYDGTLSPIVDNPDSAFMSDNMRAAVKIVAEYFPTAIISGRSRDKVYEF
SEQ ID NO:22    99  ESKGKQIVTFLDYDGTLSPIVADPDKAYMSKKMRTTLKDLARHFPTAIVSGRCLDKVYNF
SEQ ID NO:24     1  -----------------------------------RNVAKYFPAAIVSGRSRKKVLEF
SEQ ID NO:37   115  FAKGKRIALFLDYDGTLSPIVEEPDCAYMSSAMRSAVQNVAKYFPTAIISGRSRDKVYEF
SEQ ID NO:38   112  AAKGKQIVMFLDYDGTLSPIVEDPDKAFITHEMREVVKDVASNFPTAIVTGRSIEKVRSF
                    121                                                           180
                    LDYDGTLSPIVEEP
                    A-Domain
```

FIG. 1A

```
                      *          *********
SEQ ID NO:16    170   VKLTELYYAGSHGMDIVTSAAAH---ATEKC------KEANLFQPACEFLPMINEVSK
SEQ ID NO:20    171   VGVSDLCYAGSHGMDIIGPSRQSISDNHPDCISSADKQGVEVNLFQPAAEFLPMINEVLG
SEQ ID NO:22    159   VRLAELYYAGSHGMDIKGPTNKRST-------KKENEQVLFQPASEFLPMINEVYN
SEQ ID NO:24     24   VKLKELCYAGSHGMDIMTSSSAHYERNAEKG------KEANLFQPARDFLPMIDEVSK
SEQ ID NO:37    175   VNLSELYYAGSHGMDIMSPAGESLNHEHSRTVSVYE-QGKDVNLFQPASEFLPMIDKVLC
SEQ ID NO:38    172   VQVNEIYYAGSHGMDIEGPTNENSN----------GQSNERVLFQPAREFLPMIEKVVN
                                                                                240

*  *  ****  **  ****  ****  *   *     *  ***   **    ***
SEQ ID NO:16    219   CLVEVTSSIEGARVENNKFCVSVHYRNVAEKDWKVVAGLVKQVLEAFPRLKVTNGRMVLE
SEQ ID NO:20    231   LLMECTEDIEGATVENNKFCVSVHYRNVDEESWQIVGQRVYDVLKEYPRLRLTHGRKVLE
SEQ ID NO:22    208   ILVEKTKSVPGAKVENNKFCLSVHFRCVDEKSWVSLAEQVSFVLNEYPKLKLTQGRKVLE
SEQ ID NO:24     76   VLLEVTSRIEGASVEDNKFCVSVHYRNVDEKDWELVARLVNEVLEDFPRLKVTNGRMVLE
SEQ ID NO:37    234   SLIESTKDIKGVKVEDNKFCISVHYRNVEEKNWTLVAQCVDDVIRTYPKLRLTHGRKVLE
SEQ ID NO:38    221   ILEEKTKWIPGAMVENNKFCLSVHFRRVDEKRWPALAEVVKSVLIDYPKLKLTQGRKVLE
                                                                                300

** * *****  ***  ****  ***                 * *******
SEQ ID NO:16    279   VRPVIDWDKGKAVEFLLRSLGLSDSEDVVPIYIGDDRTDEDAFKVLRE-RSCGYGILVSQ
SEQ ID NO:20    291   VRPVIDWDKGKAVTFLLESLGLN-CDDVLAIYVGDDRTDEDAFKVLKEA-NKGCGILVSR
SEQ ID NO:22    268   IRPTIKWDKGKALEFLLESLGYANSDNVFPIYIGDDRTDEDAFKVLRR-RGHGVGILVSK
SEQ ID NO:24    136   VRPVIDWDKGKAVEFLLQSLGLSDSEKVIPIYIGDDRTDEDAFKVLRE-RNCGYGILVSQ
SEQ ID NO:37    294   IRPVIDWDKGKAVTFLLESLGLNNCEDVLPIYVGDDRTDEDAFKVLRDGPNHGYGILVSA
SEQ ID NO:38    281   IRPTIKWDKGQALNFLLKSLGYENSDDVVPVYIGDDRTDEDAFKVLRE-RGQGFGILVSK
                      301                                GDDRTDEDAF         360
                                                          B-Domain
```

FIG. 1B

```
SEQ ID NO:16  338 VPKDTEAFYSVRDPSEVMGFLNSLVRWKK----HPL  369
SEQ ID NO:20  349 APKESNAIYSLRDPSEVMEFLTSLAEWKSSI---QAR  382
SEQ ID NO:22  327 IPKETDASYTLQDPTEVGQFLRHLVEWKRTSSQYHKL  363
SEQ ID NO:24  195 APKETEAFYSLRDPSEVMEFLNSLVRWKK----HSL  226
SEQ ID NO:37  354 VPKDSNAFYSLRDPSEVMEFLKSLVTWKRSM---G--  385
SEQ ID NO:38  340 VPKDTNASYSLQDPSQVNKFLERLVEWKRKTVGEE--  374
              361                                       397
```

FIG. 1C

SEQUENCE LISTING

<160> NUMBER OF SEQ ID NOS: 38

<210> SEQ ID NO 1
<211> LENGTH: 1358
<212> TYPE: DNA
<213> ORGANISM: Zea mays

<400> SEQUENCE: 1

```
gcacgaggca agatcctact acactaaccg aagccaacca ccacttttga gctccatggt      60
tttagaaata tacagggcaa ctggtgatgt ggagtttgtt aggacagtat tccactctct     120
gcttaaagag catagcttct ggatgtcaga gattcataat gttgctatag cagacaatca     180
tggtcgggtc cataatttat ctcggtatca ggccaggtgg aacaaaccta ggcctgaaag     240
tgcgacaatt gatgaggaac tggcttcgaa gttgaattct atggcagcta aggaaaaact     300
gtactgcgaa attgcttcaa cggcagaatc gggatgggat tcagctctc gatggatgag      360
gaattctact gacatgacaa cattggcaac cacttacata taccctgtgg acttgaacac     420
atttctttt aagatggagc tggatattgg tgccttggct aaagtcgtag agataatgc       480
gacttcagaa tttttttaa atgcttcgaa agcacgtcat attgcaattg actctatttt      540
gtggaactct gagatggaac agtggcttga ctattggctt cctggtgatg cagactgtca     600
ggaagtacac gaatggaagc ctaactcaca gaaccgcaac atatttgctt ccaacttcgt     660
tccgctgtgg ctaaatgcat accattccga attcgtacgc tttgctgatg aggcaaaatc     720
aaacagagtc atggcgagcc tcaaggcatc tggattactt catgccgcag ggatagcaac     780
ttccctgaca aacacgagcc aacaatggga tttcccgaat ggatgggccc cactgcagca     840
tcttatagct gaggggctgc tgcattctgg atcagaggcc aaaaaactag ctgaggacat     900
tgctacgagg tgggtgagaa cgaactacgc cgcttacaaa gcaacgggtg cgatgcatga     960
gaagtacgat gttgaggctt gtggagaatc tggaggcggt ggagaataca agccccagac    1020
tggttttggc tggtccaatg gcgtggtgtt gtcattcttg gaagaattcg ggtggccaga    1080
gggcaaggaa atagcttgtt gagcggcgaa gcgctcacga cagggtggat ctggtcttgc    1140
cggagagcaa tctggttagg catcgttcat gtcacacatg tctagctacg agagtggcgc    1200
attgccttct gcagttcgtc aagtgcgttt gtgtgttctt gtttgctttt agttgcgact    1260
aggctgtaga tccttcttgt atcacaacaa tatatgtact gctactgtac cggccccggc    1320
ctcttgttta atctgaaatg ctcattgtat atcctctt                            1358
```

<210> SEQ ID NO 2
<211> LENGTH: 366
<212> TYPE: PRT
<213> ORGANISM: Zea mays

<400> SEQUENCE: 2

```
His Glu Ala Arg Ser Tyr Tyr Thr Asn Arg Ser Gln Pro Pro Leu Leu
  1               5                  10                  15

Ser Ser Met Val Leu Glu Ile Tyr Arg Ala Thr Gly Asp Val Glu Phe
             20                  25                  30

Val Arg Thr Val Phe His Ser Leu Leu Lys Glu His Ser Phe Trp Met
         35                  40                  45

Ser Glu Ile His Asn Val Ala Ile Ala Asp Asn His Gly Arg Val His
     50                  55                  60

Asn Leu Ser Arg Tyr Gln Ala Arg Trp Asn Lys Pro Arg Pro Glu Ser
```

```
                65                  70                  75                  80
Ala Thr Ile Asp Glu Glu Leu Ala Ser Lys Leu Asn Ser Met Ala Ala
                    85                  90                  95
Lys Glu Lys Leu Tyr Cys Glu Ile Ala Ser Thr Ala Glu Ser Gly Trp
                100                 105                 110
Asp Phe Ser Ser Arg Trp Met Arg Asn Ser Thr Asp Met Thr Thr Leu
                115                 120                 125
Ala Thr Thr Tyr Ile Ile Pro Val Asp Leu Asn Thr Phe Leu Phe Lys
            130                 135                 140
Met Glu Leu Asp Ile Gly Ala Leu Ala Lys Val Val Gly Asp Asn Ala
145                 150                 155                 160
Thr Ser Glu Phe Phe Leu Asn Ala Ser Lys Ala Arg His Ile Ala Ile
                165                 170                 175
Asp Ser Ile Leu Trp Asn Ser Glu Met Glu Gln Trp Leu Asp Tyr Trp
            180                 185                 190
Leu Pro Gly Asp Ala Asp Cys Gln Glu Val His Glu Trp Lys Pro Asn
        195                 200                 205
Ser Gln Asn Arg Asn Ile Phe Ala Ser Asn Phe Val Pro Leu Trp Leu
    210                 215                 220
Asn Ala Tyr His Ser Glu Phe Val Arg Phe Ala Asp Glu Ala Lys Ser
225                 230                 235                 240
Asn Arg Val Met Ala Ser Leu Lys Ala Ser Gly Leu Leu His Ala Ala
                245                 250                 255
Gly Ile Ala Thr Ser Leu Thr Asn Thr Ser Gln Gln Trp Asp Phe Pro
            260                 265                 270
Asn Gly Trp Ala Pro Leu Gln His Leu Ile Ala Glu Gly Leu Leu His
        275                 280                 285
Ser Gly Ser Glu Ala Lys Lys Leu Ala Glu Asp Ile Ala Thr Arg Trp
    290                 295                 300
Val Arg Thr Asn Tyr Ala Ala Tyr Lys Ala Thr Gly Ala Met His Glu
305                 310                 315                 320
Lys Tyr Asp Val Glu Ala Cys Gly Glu Ser Gly Gly Gly Glu Tyr
                325                 330                 335
Lys Pro Gln Thr Gly Phe Gly Trp Ser Asn Gly Val Val Leu Ser Phe
            340                 345                 350
Leu Glu Glu Phe Gly Trp Pro Glu Gly Lys Glu Ile Ala Cys
        355                 360                 365

<210> SEQ ID NO 3
<211> LENGTH: 1409
<212> TYPE: DNA
<213> ORGANISM: Glycine max

<400> SEQUENCE: 3
gcacgagcct caactcgtta ttgtacaagt acgagtcgga tatttacact gccatcgagc    60
aagtctttgg gggtgaactc gaaatggacg aagagtttga actctcgcca tggcccatca   120
ctgctgaggc tttcgccgag ggtgctgcac gtgaactctc gacatcccgc gttcaaacgg   180
cggccgagtg gaaggaacgc atggataagc gtcgtgatac gatgaatgag ctctgctgga   240
atgagggacg aggaatgttc tttgactggg ataccaaggc gcagaaacag gccaaatacg   300
agagtgttac ctgtctctgg ccactctggg ctggaaatgc gtccgaggat caggcaatga   360
agatggtcaa tatggctcta cccaagtttg aggtcgctgg cgggcttgtt tcgggaacag   420
aggagagccg aggtatcatc tcgatcgatc gaccgaatcg acagtgggat tacccttca   480
```

-continued

```
gctggccgcc gcatcagatt atgacttggg tcgggcttga gcgatacgga cacgataccc     540
acgctgcccg tcttgcgtac cgttggatct acatgatgac attgtccttt gtcgatttca     600
acggcattgt tcccgagaag tttgatgctg tcgagttgag ccacatggtg gatgccgagt     660
atggtaatca gggtactgat ttccgttatg ttccccgaga gggtttcggc tggatgaatg     720
ctgcttacca agttggattg caattcttgt ctattggtat cgccgagcg gtagctgctt      780 gtgttcctcc atgggtcttt ttcaatctcc ccgcccccga cttcccctcg gcgcgtcgtc     840
gtcgtgcgga acgcgaggcc cgcgaagccg atgctgcggc ccagggtcat ggtggacagc     900
ctaaacagca ggtacatcac gaaccgccga gtctcgagca ggctattgcc aacctcaaga     960
ttgatcttgg cacgggcacg gcgtagaatt acaagagatg ggtagacgat tgtgcaggat    1020
gctgtgaatt cttttgcgaa attcgaatgc gaaatacgag gatgattgtg aaggtctgat    1080
atcgtctctg acttgcgggt cgcgggcaag gtgtgagaca attcctcctc tacgagaatg    1140
ggcataatga ggaaaatgag aaacaggtat actcagtctg ctttttttc catcaaagaa     1200 attctcttct tttgtcattg tattcattca ctctttccgt gtgcgggata gcagcagcgg    1260
agcacggggt cgagggttgt ttagcaagag tttctctct acaagcgcat gcattacatt     1320
ttgtgacgga tgaaaaaaaa aaaaaaaaaa aaaaaaaaaa aaaaaaaaaa aaaaaaaaaa    1380
aaaaaaataa aaataaaaaa aaaaaccccc                                     1409

<210> SEQ ID NO 4
<211> LENGTH: 327
<212> TYPE: PRT
<213> ORGANISM: Glycine max

<400> SEQUENCE: 4

Thr Ser Leu Asn Ser Leu Leu Tyr Lys Tyr Glu Ser Asp Ile Tyr Thr
  1               5                  10                  15

Ala Ile Glu Gln Val Phe Gly Gly Glu Leu Glu Met Asp Glu Glu Phe
             20                  25                  30

Glu Leu Ser Pro Trp Pro Ile Thr Ala Glu Ala Phe Ala Glu Gly Ala
         35                  40                  45

Ala Arg Glu Leu Ser Thr Ser Arg Val Gln Thr Ala Ala Glu Trp Lys
     50                  55                  60

Glu Arg Met Asp Lys Arg Arg Asp Thr Met Asn Glu Leu Cys Trp Asn
 65                  70                  75                  80

Glu Gly Arg Gly Met Phe Phe Asp Trp Asp Thr Lys Ala Gln Lys Gln
                 85                  90                  95

Ala Lys Tyr Glu Ser Val Thr Cys Leu Trp Pro Leu Trp Ala Gly Asn
            100                 105                 110

Ala Ser Glu Asp Gln Ala Met Lys Met Val Asn Met Ala Leu Pro Lys
        115                 120                 125

Phe Glu Val Ala Gly Gly Leu Val Ser Gly Thr Glu Glu Ser Arg Gly
    130                 135                 140

Ile Ile Ser Ile Asp Arg Pro Asn Arg Gln Trp Asp Tyr Pro Phe Ser
145                 150                 155                 160

Trp Pro Pro His Gln Ile Met Thr Trp Val Gly Leu Glu Arg Tyr Gly
                165                 170                 175

His Asp Thr His Ala Ala Arg Leu Ala Tyr Arg Trp Ile Tyr Met Met
            180                 185                 190

Thr Leu Ser Phe Val Asp Phe Asn Gly Ile Val Pro Glu Lys Phe Asp
        195                 200                 205
```

```
Ala Val Glu Leu Ser His Met Val Asp Ala Glu Tyr Gly Asn Gln Gly
    210                 215                 220

Thr Asp Phe Arg Tyr Val Pro Arg Glu Gly Phe Gly Trp Met Asn Ala
225                 230                 235                 240

Ala Tyr Gln Val Gly Leu Gln Phe Leu Ser Ile Gly Met Arg Arg Ala
                245                 250                 255

Val Ala Ala Cys Val Pro Pro Trp Val Phe Asn Leu Pro Ala Pro
            260                 265                 270

Asp Phe Pro Ser Ala Arg Arg Arg Ala Glu Arg Glu Ala Arg Glu
            275                 280                 285

Ala Asp Ala Ala Gln Gly His Gly Gly Gln Pro Lys Gln Gln Val
    290                 295                 300

His His Glu Pro Pro Ser Leu Glu Gln Ala Ile Ala Asn Leu Lys Ile
305                 310                 315                 320

Asp Leu Gly Thr Gly Thr Ala
                325

<210> SEQ ID NO 5
<211> LENGTH: 749
<212> TYPE: DNA
<213> ORGANISM: Zea mays

<400> SEQUENCE: 5
ccacgcgtcc gccaactacc tgctggccaa tttctcgtgc ctgccggtgt accttcccac     60
cgacctccac caccgcttct accacggatt ctgcaagcac tacctctggc cgctcctcca    120
ctacctcctc ccgctgacgc cgtcctcgct cggtggcctc cctttccagc gaacgctcta    180
ccactccttc ctctcggcaa acagggcgtt cgccgaccgc ctcaccgagg tgctgtcccc    240
cgacgaggac ctcgtctgga tccacgatta ccacctcctc gcgctcccga ccttcctccg    300
caagcgcttc ccgcgcgcca aggtcggatt cttcctccac tcacccttcc cctcgtcgga    360
gatcttccgt acgatccccg tgcgggatga cctcgtccgc gcactcctca acgccgacct    420
cgtcggcttc cacaccttcg actacgcgcg ccacttcctg tccgcgtgct cgcggctgct    480
cggcctcgac taccagtcca agcgcggcta catcggcatc gagtattacg ccgcaccgt    540
gactgtcaag atactccccg ttgggatcga catgggcag ctcagatcgg tggtctcggc    600
gccggagacg gaggacgcgg tgcggcgggt gacagaggcg tacaagggaa ggcgcctcat    660
ggtaggcgtc gacgacgtcg atctgttcaa ggggatcggg ctcaagttcc tggcgatgga    720
gcagctgctc gtggagcacc gggagctcc                                      749

<210> SEQ ID NO 6
<211> LENGTH: 249
<212> TYPE: PRT
<213> ORGANISM: Zea mays

<400> SEQUENCE: 6

His Ala Ser Ala Asn Tyr Leu Leu Ala Asn Phe Ser Cys Leu Pro Val
  1               5                  10                  15

Tyr Leu Pro Thr Asp Leu His His Arg Phe Tyr His Gly Phe Cys Lys
                20                  25                  30

His Tyr Leu Trp Pro Leu Leu His Tyr Leu Leu Pro Leu Thr Pro Ser
            35                  40                  45

Ser Leu Gly Gly Leu Pro Phe Gln Arg Thr Leu Tyr His Ser Phe Leu
    50                  55                  60
```

-continued

```
Ser Ala Asn Arg Ala Phe Ala Asp Arg Leu Thr Glu Val Leu Ser Pro
 65                  70                  75                  80

Asp Glu Asp Leu Val Trp Ile His Asp Tyr His Leu Leu Ala Leu Pro
                 85                  90                  95

Thr Phe Leu Arg Lys Arg Phe Pro Arg Ala Lys Val Gly Phe Phe Leu
            100                 105                 110

His Ser Pro Phe Pro Ser Ser Glu Ile Phe Arg Thr Ile Pro Val Arg
        115                 120                 125

Asp Asp Leu Val Arg Ala Leu Leu Asn Ala Asp Leu Val Gly Phe His
130                 135                 140

Thr Phe Asp Tyr Ala Arg His Phe Leu Ser Ala Cys Ser Arg Leu Leu
145                 150                 155                 160

Gly Leu Asp Tyr Gln Ser Lys Arg Gly Tyr Ile Gly Ile Glu Tyr Tyr
                165                 170                 175

Gly Arg Thr Val Thr Val Lys Ile Leu Pro Val Gly Ile Asp Met Gly
            180                 185                 190

Gln Leu Arg Ser Val Val Ser Ala Pro Glu Thr Glu Asp Ala Val Arg
        195                 200                 205

Arg Val Thr Glu Ala Tyr Lys Gly Arg Arg Leu Met Val Gly Val Asp
    210                 215                 220

Asp Val Asp Leu Phe Lys Gly Ile Gly Leu Lys Phe Leu Ala Met Glu
225                 230                 235                 240

Gln Leu Leu Val Glu His Arg Glu Leu
                245
```

<210> SEQ ID NO 7
<211> LENGTH: 3083
<212> TYPE: DNA
<213> ORGANISM: Oryza sativa

<400> SEQUENCE: 7

```
gcacgaggcg gatgtcgcgg gtgatgacgg tgcccgggac gctgtcggag ctggacgggg     60
aggacgactc ggagcacgcg gcgacgaaca gcgtcgcctc cgacgtgccc tcgtcggtgg    120
cggggatcg agtcatagtg gtctccaacc agctgcccgt cgtcgcacgc cgccgtcccg    180
acggccgcgg gtggtccttc tcatgggacg acgactcgct gctcctccag ctccgcgacg    240
gcattcccga tgagatggag gtgttcttcg tcggttccct ccgcgccgaa atccccgtcg    300
ccgaccagga gaggtctccc aggcgctgc tcgatcgctt ccgatgtgct ccggtgttcc    360
tccccgaccc cctcaacgaa cggttttacc accgcttctg caagcgccac ctatggcctc    420
tgttccacta catgctccct ttctcctcct ccgcatcccc gagtccctcc tcctcctcct    480
cctcctcctc ctcccctca tcctcatccg gcagtggcca cttcgaccgc ggcgcgtggg    540
aggcctacgt gctcgcgaac aagttcttct tcgagaaggt cgtggaggtc atcaacccag    600
aagacgacta cgtatgggtt cacgactacc atctcatggc gctgcccacc ttccttcgcc    660
gccgcttcaa ccgcctgcgc atcggcttct tcctccacag ccccttcccc tcgtcggaga    720
tctaccggac cctccctgtt cgcgaggaga tcctaaaggc gctgctcaat gtgaccttta    780
ttggattcca cacttttgac tatgccagac atttcctctc ttgttgtagt aggatgctgg    840
gaattgaata ccagtcaaag cgtggataca ttggttggga ttactttggg cgtaccgttg    900
ggatcaaaat catgccagtg ggagttcata tgggtcaatt gaagacggtt ctgagcttgc    960
ccgacaggga atggagggtc tccgagctgc agcagcaatt tgaggggaag actgtgttgc   1020
tcggtgtgga tgacatggat atcttcaagg gtatcaactt gaagcttctt gccttcgaga   1080
```

```
atatgttgag acacatccc aagtggcagg ggcgggcagt gttggtgcaa attgctaatc    1140
cggcccgtgg aaagggtaag gatcttgaag ccatccaggc tgagattcat gagagctgca    1200
agaggattaa tggagagttt ggccagtcag gatacagccc tgttgtcttc attgaccgtg    1260
atgtgtcaag tgtggagaag attgcctact acacaatagc agaatgtgtg gtggtgactg    1320
ctgtgaggga tgggatgaac ttgacaccat atgaatatat tgtctgtagg cagggggtctg    1380
actccacatc agaagtgaat ggaccaaaga gagcatgct ggtggtatca gaattcattg      1440
ggtgctcacc atctctgagt ggtgctatcc gggttaaccc atggaatata gaggcaaccg     1500
cagaggcact gaatgaggcc atatcaatgt cggaacagga gaaacaccta aggcatgaga     1560
aacattaccg ttatgtcagc acccacgatg ttgcttattg gtcgaaaagt ttcatccaag     1620
atttggagag ggcttgcaag gaccacttca ggaggacatg ttggggcatc gggttggggt     1680
ttggttttag ggtggtggcc ttagatcccc atttcacaaa gcttaacatg gattcaattg     1740
ttatggctta tgagcggtca gagagtaggg ctatatttct tgattatgat ggaacactgg    1800
tgccacagac ttccatcagt aggacaccta gtgcggaagt tttgaggatc atcaataccc     1860
tgtgctcaga taggaggaac aaagttttc ttgtcagtgg gagacgcagg gacaaattgg      1920
gagaatggtt ttcctcttgt ccagatctgg gcattgcagc agagcatggt tacttcttaa    1980
ggtggactag agacgaagag tggcaaacat gtacccagac ctctgacttc gggtggatgg    2040
aaatggccaa gccagtgatg aatctgtata cagaagcaac tgatggatct tacattgatc    2100
ctaaggaaag tgctttggtg tggcatcacc aggatgctga cccaggattt ggatcctccc    2160
aggcaaagga gttacttgat catctggaaa gtgtattagc aaatgaacct gtttctgtca    2220
aaagtggcca gttcattgtt gaagtcaaac ctcagggagt aagcaaggga gtagtagctg    2280
agaagatact cgtctcaatg aaggagagag gaaagcaggc tgactttgta ttatgcattg    2340
gtgatgacag gtcggatgag gacatgtttg aaaacattgc tgataccatt aaaaagggta    2400
tggttgctac aaacacatca ttgtttgcat gcactgtggg acaaaaacca agcaaggcca    2460
aattttacct ggatgatacg tttgaagtgg tcaccatgct gagcgcactg gcagatgcta    2520
ctgaaccaga acctgagact gatcttaccg atgagtttga tgaactggcc gtgtctgtct    2580
cctcagttga tattgatgat gaacaaacgc ccagtgataa actgatcgga ggatagtagt    2640
caaggttgct tatatctgca gattgtcatg attaattcaa ccatctctat acaattttg     2700
atgaatgtga aagctgggta ctcaaagaat gactaacacc aggccctacg aatgctccag    2760
tgtgaagtta ataccgtgga gtgctcgatt ctccactggg ggcaaaagcc aatacaatct    2820
tgtgctggaa aagtaggtcc atatgtccat agctgacttc acttttcttt gcacgtttct    2880
gttttaactt tttccatatc aagtaaaatg gaaagcttca cggaaggcaa gtgaatgtat    2940
gtatggcttg cacatgagaa agtttccacg tgcagcttgt gatgatgtga tcccccccgca   3000
ttaacgcgta acgcggtgca ttctttttt gtactcttga ggtagtagca aatgtgaatg     3060
aagtttgtgc tcgttgtttg att                                            3083
```

<210> SEQ ID NO 8
<211> LENGTH: 877
<212> TYPE: PRT
<213> ORGANISM: Oryza sativa

<400> SEQUENCE: 8

Thr Arg Arg Met Ser Arg Val Met Thr Val Pro Gly Thr Leu Ser Glu
1               5                   10                  15

```
Leu Asp Gly Glu Asp Asp Ser Glu His Ala Ala Thr Asn Ser Val Ala
            20                  25                  30

Ser Asp Val Pro Ser Ser Val Ala Gly Asp Arg Val Ile Val Val Ser
        35                  40                  45

Asn Gln Leu Pro Val Val Ala Arg Arg Pro Asp Gly Arg Gly Trp
    50                  55                  60

Ser Phe Ser Trp Asp Asp Asp Ser Leu Leu Gln Leu Arg Asp Gly
65                  70                  75                  80

Ile Pro Asp Glu Met Glu Val Phe Phe Val Gly Ser Leu Arg Ala Glu
                85                  90                  95

Ile Pro Val Ala Asp Gln Glu Val Ser Gln Ala Leu Leu Asp Arg
                100                 105                 110

Phe Arg Cys Ala Pro Val Phe Leu Pro Asp Pro Leu Asn Glu Arg Phe
        115                 120                 125

Tyr His Arg Phe Cys Lys Arg His Leu Trp Pro Leu Phe His Tyr Met
        130                 135                 140

Leu Pro Phe Ser Ser Ser Ala Ser Pro Ser Pro Ser Ser Ser Ser Ser
145                 150                 155                 160

Ser Ser Ser Ser Pro Ser Ser Ser Ser Gly Ser Gly His Phe Asp Arg
                165                 170                 175

Gly Ala Trp Glu Ala Tyr Val Leu Ala Asn Lys Phe Phe Glu Lys
        180                 185                 190

Val Val Glu Val Ile Asn Pro Glu Asp Asp Tyr Val Trp Val His Asp
        195                 200                 205

Tyr His Leu Met Ala Leu Pro Thr Phe Leu Arg Arg Arg Phe Asn Arg
        210                 215                 220

Leu Arg Ile Gly Phe Phe Leu His Ser Pro Phe Pro Ser Ser Glu Ile
225                 230                 235                 240

Tyr Arg Thr Leu Pro Val Arg Glu Glu Ile Leu Lys Ala Leu Leu Asn
                245                 250                 255

Cys Asp Leu Ile Gly Phe His Thr Phe Asp Tyr Ala Arg His Phe Leu
                260                 265                 270

Ser Cys Cys Ser Arg Met Leu Gly Ile Glu Tyr Gln Ser Lys Arg Gly
        275                 280                 285

Tyr Ile Gly Leu Asp Tyr Phe Gly Arg Thr Val Gly Ile Lys Ile Met
        290                 295                 300

Pro Val Gly Val His Met Gly Gln Leu Lys Thr Val Leu Ser Leu Pro
305                 310                 315                 320

Asp Arg Glu Trp Arg Val Ser Glu Leu Gln Gln Phe Glu Gly Lys
                325                 330                 335

Thr Val Leu Leu Gly Val Asp Asp Met Asp Ile Phe Lys Gly Ile Asn
                340                 345                 350

Leu Lys Leu Leu Ala Phe Glu Asn Met Leu Arg Thr His Pro Lys Trp
        355                 360                 365

Gln Gly Arg Ala Val Leu Val Gln Ile Ala Asn Pro Ala Arg Gly Lys
    370                 375                 380

Gly Lys Asp Leu Glu Ala Ile Gln Ala Glu Ile His Glu Ser Cys Lys
385                 390                 395                 400

Arg Ile Asn Gly Glu Phe Gly Gln Ser Gly Tyr Ser Pro Val Val Phe
                405                 410                 415

Ile Asp Arg Asp Val Ser Ser Val Glu Lys Ile Ala Tyr Tyr Thr Ile
                420                 425                 430
```

-continued

```
Ala Glu Cys Val Val Thr Ala Val Arg Asp Gly Met Asn Leu Thr
    435                 440                 445
Pro Tyr Glu Tyr Ile Val Cys Arg Gln Gly Ser Asp Ser Thr Ser Glu
    450                 455                 460
Val Asn Gly Pro Lys Lys Ser Met Leu Val Ser Glu Phe Ile Gly
465                 470                 475                 480
Cys Ser Pro Ser Leu Ser Gly Ala Ile Arg Val Asn Pro Trp Asn Ile
                485                 490                 495
Glu Ala Thr Ala Glu Ala Leu Asn Glu Ala Ile Ser Met Ser Glu Gln
            500                 505                 510
Glu Lys His Leu Arg His Glu Lys His Tyr Arg Tyr Val Ser Thr His
        515                 520                 525
Asp Val Ala Tyr Trp Ser Lys Ser Phe Ile Gln Asp Leu Glu Arg Ala
    530                 535                 540
Cys Lys Asp His Phe Arg Arg Thr Cys Trp Gly Ile Gly Leu Gly Phe
545                 550                 555                 560
Gly Phe Arg Val Val Ala Leu Asp Pro His Phe Thr Lys Leu Asn Met
                565                 570                 575
Asp Ser Ile Val Met Ala Tyr Glu Arg Ser Glu Ser Arg Ala Ile Phe
            580                 585                 590
Leu Asp Tyr Asp Gly Thr Leu Val Pro Gln Thr Ser Ile Ser Arg Thr
        595                 600                 605
Pro Ser Ala Glu Val Leu Arg Ile Ile Asn Thr Leu Cys Ser Asp Arg
    610                 615                 620
Arg Asn Lys Val Phe Leu Val Ser Gly Arg Arg Asp Lys Leu Gly
625                 630                 635                 640
Glu Trp Phe Ser Ser Cys Pro Asp Leu Gly Ile Ala Ala Glu His Gly
                645                 650                 655
Tyr Phe Leu Arg Trp Thr Arg Asp Glu Glu Trp Gln Thr Cys Thr Gln
            660                 665                 670
Thr Ser Asp Phe Gly Trp Met Glu Met Ala Lys Pro Val Met Asn Leu
        675                 680                 685
Tyr Thr Glu Ala Thr Asp Gly Ser Tyr Ile Asp Pro Lys Glu Ser Ala
    690                 695                 700
Leu Val Trp His His Gln Asp Ala Asp Pro Gly Phe Gly Ser Ser Gln
705                 710                 715                 720
Ala Lys Glu Leu Leu Asp His Leu Glu Ser Val Leu Ala Asn Glu Pro
                725                 730                 735
Val Ser Val Lys Ser Gly Gln Phe Ile Val Glu Val Lys Pro Gln Gly
            740                 745                 750
Val Ser Lys Gly Val Val Ala Glu Lys Ile Leu Val Ser Met Lys Glu
        755                 760                 765
Arg Gly Lys Gln Ala Asp Phe Val Leu Cys Ile Gly Asp Asp Arg Ser
    770                 775                 780
Asp Glu Asp Met Phe Glu Asn Ile Ala Asp Thr Ile Lys Lys Gly Met
785                 790                 795                 800
Val Ala Thr Asn Thr Ser Leu Phe Ala Cys Thr Val Gly Gln Lys Pro
                805                 810                 815
Ser Lys Ala Lys Phe Tyr Leu Asp Asp Thr Phe Glu Val Val Thr Met
            820                 825                 830
Leu Ser Ala Leu Ala Asp Ala Thr Glu Pro Glu Pro Glu Thr Asp Leu
        835                 840                 845
Thr Asp Glu Phe Asp Glu Leu Ala Val Ser Val Ser Ser Val Asp Ile
```

```
                850              855              860
Asp Asp Glu Gln Thr Pro Ser Asp Lys Leu Ile Gly Gly
865              870              875

<210> SEQ ID NO 9
<211> LENGTH: 3157
<212> TYPE: DNA
<213> ORGANISM: Oryza sativa

<400> SEQUENCE: 9
gcacgagcgc tgtcggagct ggacgacgag gacgacgagc cggcggcgac gagcagcgtc       60
gcctccgacg tgccctcgtc ggcggcgtgc gagcgcctca tcgtcgtggc gaaccagctc      120
cccgtggtgg cgcggcggag gccgggcgcc cggcggggg gtgggcgtt ctcgtgggac        180 gacgactcgc tcctcctccg cctccgcgac ggcgtccccg acgagatgga ggtgctcttc      240
atcggcacgc tccgcgccga cgtgcccgcc tgcgagcagg acgaggtgtc gcagagcctc      300
atcgatggat tcggatgcgc accctgttc ctccccgcgg ggctctacga ccgattctac      360
cagcacttct gcaagggtta cctatggccg ctgttccact acatgctccc cttcgcctcc      420
gccttgccgg cggccgcatc cggcgatggc cggtttgacc gcggcgcgtg ggaggcctac      480
gtgctcgcca acaaatactt cttcgagaag gtggtcgagg tcatcaaccc ggaggacgac      540
tacgtttggg tccacgatta ccacctcatg gcgctgccca ccttcctccg ccgccgcttc      600
aatcgcctcc gcatcgggtt cttcctccac agccccttc cctcatcgga gatctaccgc      660
tcgctgcccg tccgagagga gatcctaaga acgctgctta attgcgatct cattggattc      720
cacacattcg attatgcgag gcacttccta tcttgctgta gtaggatgct ggggatagag      780
taccagtcaa agcgtggata cattggattg gattactttg gccgcactgt tggaatcaag      840
atcatgccag tgggaatcca tatgggtcaa ttgcaatcag tgttgcgatt gtccgagaaa      900
gaaaagaagg ttgctgagct gcggcagcaa ttcgagggca gtccgtgtt acttggtgtg       960 gatgatatgg atatcttcaa gggaatcaac ttaaaacttc ttgcgtttga gaatatgctg     1020
aggacgcatc ccaagtggaa gggaagagct gtgttggtgc agattgcaaa cccagcacga     1080
gggaagggaa aggatctgga ggctgtccag gctgagattc gggagagttg tgatagaatt     1140
aacaaggagt ttggccagtc aggttacagt ccagtgattt tcattgacca gagcgtgcca     1200
agtgcggtga ggcttgcata ttatacggtt gctgagtgtg ttgtggtgac ggctgtgagg     1260
gatgggatga atttgacccc catatgaatac attgtctgcc gggaggggat acctggctct     1320
gagtgtgcac cagaggtgag tggaccaaag aagagcatgt tggttgtgtc ggagtttatt     1380
ggttgctcac cttcactgag tggagccatt cgtgttaacc cgtggaatat cgaggcaact     1440
gcagaggcac tgaatgaggc catctcaatg tcagagcgtg aaaagcagct gaggcacgaa     1500
aaacattacc gttatgtcag cacccatgat gttgcatatt ggtctaagag ctttgtacag     1560
gacctggaga gggcttgcaa ggatcacttt aggaaaccat gctggggcat ggattggga      1620 tttggcttca gggtggtagc cctagaccca catttcacaa agcttaattt cgaatcaatt     1680
ataatgtcct atgagagatc aaagagtagg gctatatttc tcgactatga tggcacattg     1740
gtgccacagg cttcgctcaa caagaatcca agtgaagaat tactgaggat cattaatacc     1800
ctatgcgcag atagaaataa caccgtgttc attgtcagcg ggagaagcaa ggatgacttg     1860
agcaaaaagc ttatctcatg tccaaagcta ggcattgccg cagagcatgg ctacttctta     1920
aggtggacta gagatgaaga atggcaaacc actgcacaga cctcagattt tggatggatg     1980
```

-continued

```
caaatggcga agccagtgat ggatctttat actgaatcaa ctgacggatc caccattgag   2040
actaaagaaa ctgcactggt gtggcaccat caggatgctg accaaggttt tggctcttcc   2100
caggcaaagg aaatgcttga tcacttggaa agtgtattag caaatgaacc agtctcagtc   2160
aagagtggcc aattcattgt tgaagtcaaa cctcagggtg ttaccaaagg gctcatagct   2220
gagaaagtac tcacatcaat gaaggagaag gggcaactgg cagattttgt attatgcatt   2280
ggtgatgaca ggtcagatga ggatatgttt gaaaatattg ccgatgtcat gaaaaggagc   2340
attgttgcac caaaaactcc actgtttgca tgtactgtgg ccagaagcc aagcaaagct    2400 aggttttacc tggatgatac atttgaagtc gtcaccatgt tgagttcact ggcggatgct   2460
tcagaaccag accttatggc agacttggaa gatgacttgg ccacatcagt ctcatcaata   2520
gaaataagtg acagagtggt atcttttagt aatttaagga cagaaggatc ttagtctggt   2580
gtttctgcgt tgcttttctc gccgaaaaag ttctgttgga actgagtgag ggagtgttaa   2640
gcaagatgaa acactgcaag attaaagatg ctacagggca aggaagtcga attcttgggt   2700
tcatgattca ttttggtgaa gatgagggta agggattaaa acatgtagct gcaaatattc   2760
tgaagtccgg aaagagatta cagtttgagt agctcccaaa tagcctcatt atgcgttttg   2820
ttacggcggc atttactacc agtcgctgct acgaagattc ttatgttcat agctgacctg   2880
ccatgttctt tccatttgaa tactatcccc aaggctaagt aggaagcatc ggcgtggcag   2940
aagtgcatcg gtgcaatatg ggggaatatg agggtaaatc ttgtgacagg ttaactgcag   3000
cttgtgattt cttgcttgtt aacctggtta acagaaatcg tctagtaggg aaaaaactag   3060
tgatgctttt cgtttacttg taatgttgtg gcaatgtgga ggatgacatt tgattcattg   3120
tttgacagca ttatctgtat catccttata tgtagct                            3157
```

<210> SEQ ID NO 10
<211> LENGTH: 857
<212> TYPE: PRT
<213> ORGANISM: Oryza sativa

<400> SEQUENCE: 10

```
Ala Arg Ala Leu Ser Glu Leu Asp Asp Glu Asp Asp Glu Pro Ala Ala
  1               5                  10                  15

Thr Ser Ser Val Ala Ser Asp Val Pro Ser Ser Ala Ala Cys Glu Arg
             20                  25                  30

Leu Ile Val Val Ala Asn Gln Leu Pro Val Val Ala Arg Arg Arg Pro
         35                  40                  45

Gly Ala Ala Gly Gly Trp Ala Phe Ser Trp Asp Asp Asp Ser Leu
     50                  55                  60

Leu Leu Arg Leu Arg Asp Gly Val Pro Asp Glu Met Glu Val Leu Phe
 65                  70                  75                  80

Ile Gly Thr Leu Arg Ala Asp Val Pro Ala Cys Glu Gln Asp Glu Val
                 85                  90                  95

Ser Gln Ser Leu Ile Asp Gly Phe Gly Cys Ala Pro Val Phe Leu Pro
            100                 105                 110

Ala Gly Leu Tyr Asp Arg Phe Tyr Gln His Phe Cys Lys Gly Tyr Leu
        115                 120                 125

Trp Pro Leu Phe His Tyr Met Leu Pro Phe Ala Ser Ala Leu Pro Ala
    130                 135                 140

Ala Ala Ser Gly Asp Gly Arg Phe Asp Arg Gly Ala Trp Glu Ala Tyr
145                 150                 155                 160

Val Leu Ala Asn Lys Tyr Phe Phe Glu Lys Val Val Glu Val Ile Asn
```

```
                    165                 170                 175
Pro Glu Asp Asp Tyr Val Trp Val His Asp Tyr His Leu Met Ala Leu
            180                 185                 190
Pro Thr Phe Leu Arg Arg Arg Phe Asn Arg Leu Arg Ile Gly Phe Phe
        195                 200                 205
Leu His Ser Pro Phe Pro Ser Ser Glu Ile Tyr Arg Ser Leu Pro Val
    210                 215                 220
Arg Glu Glu Ile Leu Arg Thr Leu Leu Asn Cys Asp Leu Ile Gly Phe
225                 230                 235                 240
His Thr Phe Asp Tyr Ala Arg His Phe Leu Ser Cys Cys Ser Arg Met
                245                 250                 255
Leu Gly Ile Glu Tyr Gln Ser Lys Arg Gly Tyr Ile Gly Leu Asp Tyr
            260                 265                 270
Phe Gly Arg Thr Val Gly Ile Lys Ile Met Pro Val Gly Ile His Met
        275                 280                 285
Gly Gln Leu Gln Ser Val Leu Arg Leu Ser Glu Lys Glu Lys Lys Val
    290                 295                 300
Ala Glu Leu Arg Gln Gln Phe Glu Gly Lys Ser Val Leu Leu Gly Val
305                 310                 315                 320
Asp Asp Met Asp Ile Phe Lys Gly Ile Asn Leu Lys Leu Leu Ala Phe
                325                 330                 335
Glu Asn Met Leu Arg Thr His Pro Lys Trp Lys Gly Arg Ala Val Leu
            340                 345                 350
Val Gln Ile Ala Asn Pro Ala Arg Gly Lys Gly Lys Asp Leu Glu Ala
        355                 360                 365
Val Gln Ala Glu Ile Arg Glu Ser Cys Asp Arg Ile Asn Lys Glu Phe
    370                 375                 380
Gly Gln Ser Gly Tyr Ser Pro Val Ile Phe Ile Asp Gln Ser Val Pro
385                 390                 395                 400
Ser Ala Val Arg Leu Ala Tyr Tyr Thr Val Ala Glu Cys Val Val Val
                405                 410                 415
Thr Ala Val Arg Asp Gly Met Asn Leu Thr Pro Tyr Glu Tyr Ile Val
            420                 425                 430
Cys Arg Glu Gly Ile Pro Gly Ser Glu Cys Ala Pro Glu Val Ser Gly
        435                 440                 445
Pro Lys Lys Ser Met Leu Val Val Ser Glu Phe Ile Gly Cys Ser Pro
    450                 455                 460
Ser Leu Ser Gly Ala Ile Arg Val Asn Pro Trp Asn Ile Glu Ala Thr
465                 470                 475                 480
Ala Glu Ala Leu Asn Glu Ala Ile Ser Met Ser Glu Arg Glu Lys Gln
                485                 490                 495
Leu Arg His Glu Lys His Tyr Arg Tyr Val Ser Thr His Asp Val Ala
            500                 505                 510
Tyr Trp Ser Lys Ser Phe Val Gln Asp Leu Glu Arg Ala Cys Lys Asp
        515                 520                 525
His Phe Arg Lys Pro Cys Trp Gly Ile Gly Leu Gly Phe Gly Phe Arg
    530                 535                 540
Val Val Ala Leu Asp Pro His Phe Thr Lys Leu Asn Phe Glu Ser Ile
545                 550                 555                 560
Ile Met Ser Tyr Glu Arg Ser Lys Ser Arg Ala Ile Phe Leu Asp Tyr
                565                 570                 575
Asp Gly Thr Leu Val Pro Gln Ala Ser Leu Asn Lys Asn Pro Ser Glu
            580                 585                 590
```

-continued

Glu Leu Leu Arg Ile Ile Asn Thr Leu Cys Ala Asp Arg Asn Asn Thr
            595                 600                 605

Val Phe Ile Val Ser Gly Arg Ser Lys Asp Asp Leu Ser Lys Lys Leu
        610                 615                 620

Ile Ser Cys Pro Lys Leu Gly Ile Ala Ala Glu His Gly Tyr Phe Leu
625                 630                 635                 640

Arg Trp Thr Arg Asp Glu Glu Trp Gln Thr Thr Ala Gln Thr Ser Asp
                645                 650                 655

Phe Gly Trp Met Gln Met Ala Lys Pro Val Met Asp Leu Tyr Thr Glu
            660                 665                 670

Ser Thr Asp Gly Ser Thr Ile Glu Thr Lys Glu Thr Ala Leu Val Trp
        675                 680                 685

His His Gln Asp Ala Asp Gln Gly Phe Gly Ser Ser Gln Ala Lys Glu
    690                 695                 700

Met Leu Asp His Leu Glu Ser Val Leu Ala Asn Glu Pro Val Ser Val
705                 710                 715                 720

Lys Ser Gly Gln Phe Ile Val Glu Val Lys Pro Gln Gly Val Thr Lys
                725                 730                 735

Gly Leu Ile Ala Glu Lys Val Leu Thr Ser Met Lys Glu Lys Gly Gln
            740                 745                 750

Leu Ala Asp Phe Val Leu Cys Ile Gly Asp Asp Arg Ser Asp Glu Asp
        755                 760                 765

Met Phe Glu Asn Ile Ala Asp Val Met Lys Arg Ser Ile Val Ala Pro
    770                 775                 780

Lys Thr Pro Leu Phe Ala Cys Thr Val Gly Gln Lys Pro Ser Lys Ala
785                 790                 795                 800

Arg Phe Tyr Leu Asp Asp Thr Phe Glu Val Val Thr Met Leu Ser Ser
                805                 810                 815

Leu Ala Asp Ala Ser Glu Pro Asp Leu Met Ala Asp Leu Glu Asp Asp
            820                 825                 830

Leu Ala Thr Ser Val Ser Ser Ile Glu Ile Ser Asp Arg Val Val Ser
        835                 840                 845

Phe Ser Asn Leu Arg Thr Glu Gly Ser
    850                 855

<210> SEQ ID NO 11
<211> LENGTH: 2538
<212> TYPE: DNA
<213> ORGANISM: Glycine max

<400> SEQUENCE: 11
gcacgaggct gaacaggatg atgtatcaca gtatttattg gataaattca aatgtgtgcc      60 gacttttta cccgctgacg ttttggcaaa atttttatgac ggcttctgta acggcagtt     120 atggccactt tttcattata tgttaccatt tcaacagat aaaagccacc gatttgatcg     180
ttctttgtgg aagcttacg tgctggcaaa caagcttttt tttcagaagg tagttgaaat     240
aataaaccca gaggatgatt acatttggat tcatgattat catttgatgg tgctgccaac     300
ttttataaga aggcgtttta acagggttaa atgggatttt tccctgcata gccccttccc     360
atcatcagag atatacagga ctcttccggt cagggaagag atactgaaag ctttactaaa     420
ctctgatatc atcggattcc ataccttga ctatgctcgt catttccttt cctgttgcag     480
tcgtatgttg ggtctggagt atcagtcaaa gaggggttat ttaggattgg agtattatgg     540
aaggacaatc agtattaaga ttatgcctgt tgggattcac atgggtcgaa ttgagtcagt     600

```
tatgagaatg gcagatgagg aatgcaaggt aagggagctc aaacagaaat ttgaaggaaa    660
aaccatcttg cttggtattg atgatatgga catttttaaa ggcataaatt tgaagatttt    720
ggctatggag cagatgctca gacagcatcc caaatggcaa ggaagagctg ttctggtcca    780
gatagttaat cctgctagag gtaaagggat acatctggag gagatacatg ctgaaataca    840
agaaagctgc aacaggatca acagagtgtt tgggagacct ggttatgaac ctattgtttt    900
tattgataga gcagttccta ttgctgaaaa agttgcttat tactgcattg ctgagtgtgt    960
tattgtcaca gctgtaaggg atggaatgaa cctaactcct tatgagtata ttgcatgtag   1020
acagggaata tctggttctg aatcatgttc caatgtcaat gaccctaaga gagtatgct    1080
agtaatatca gaatttattg ggtgttctcc atcacttagt ggggcaatcc gtgtcaatcc   1140
atggaatgtt gaagcaactt cagaggcaat gaatgaggcc atctcaactg gtgatggaga   1200
gaaacagttg cggcacgaga agcattaccg ttatgtcagc actcatgatg tggcttactg   1260
gtcacgtagt ttcttgcaag acatggagcg ggcttgcaca gaccttctaa ggaaaagatg   1320
ttggggaata ggtcttagct ttggatttag agttgtggca cttgacccta attttaaaaa   1380
gctctcaatc gatgctatgg tttcagctta caagagggca agaatagggc cattttgtt    1440
ggactatgat ggtactgtga tgccacagaa ctccattaat aagagtccaa gcaaggaggt   1500
cttgtctatt ttggaatcac ttagtgaaga ccccaaaaat gttgttttca ttgttagtgg   1560
acggggagg aatagcttaa gtgactggtt taattcctgt gaaaaacttg gaattgctgc    1620
agaacatggg tacttcttga gatggtccca aatcgagaa tggaaaattt gtggtaagag    1680
ctccgacttt ggatggatgc agattgctga acctgtaatg aaactctata cagaggcgac   1740
tgatggttcc tctattgaaa gaaaagaaag tgctttggtc tggcaatacc gtgatgcaga   1800
ccttggtttt ggatctgctc aggctaagga aatgttagat catctagaaa gtgttttggc   1860
caatgagcct gttgctgtga gagtggcca gtttattgtt gaagtaaaac cccaggatgt    1920
gagcaaaggc ttagtcgccg agaagatatt ttcgtcaatg gacgggaagg gcaaacaggc   1980
cgactttgtg ttgtgtgttg gtgatgacag atcagatgag gacatgtttg agatagttag   2040
tagtgccatc tcaaggaata ttcttgccac caatgcttct gtgtttgctt gcacggttgg   2100
acaaaaacca gcaaagcaa agtattattt ggatgataca actgaggtaa caagcatgtt    2160
ggaatctttg gctgaagaat cagatgcttc accctacata aagaaactg gagattcctc    2220
tcggaggcaa gtgtgagttg aggttgaggt ttctcttatt ttaggtgatg atttttttt    2280
ttaattggga tgtaatattc gtggtgatat ttggggcgtt tgcagagtat gttttcataa   2340
tattttttt tctttttgg tttttcttct attatatatt acatatattt ttgggagaat     2400
cccgtcatta ttttctgttg cagtcattga tagttttatt atttagttg tggtgtagca    2460
gataacaagg atgctaattt tgatttttt atattctata acaaggaag aaaagagtga    2520
aagctcttct tgcttggc                                                 2538

<210> SEQ ID NO 12
<211> LENGTH: 744
<212> TYPE: PRT
<213> ORGANISM: Glycine max

<400> SEQUENCE: 12

His Glu Ala Glu Gln Asp Asp Val Ser Gln Tyr Leu Leu Asp Lys Phe
 1               5                  10                  15

Lys Cys Val Pro Thr Phe Leu Pro Ala Asp Val Leu Ala Lys Phe Tyr
```

-continued

```
                    20                  25                  30
Asp Gly Phe Cys Lys Arg Gln Leu Trp Pro Leu Phe His Tyr Met Leu
                35                  40                  45
Pro Phe Ser Thr Asp Lys Ser His Arg Phe Asp Arg Ser Leu Trp Glu
            50                  55                  60
Ala Tyr Val Leu Ala Asn Lys Leu Phe Phe Gln Lys Val Val Glu Ile
         65                  70                  75                  80
Ile Asn Pro Glu Asp Asp Tyr Ile Trp Ile His Asp Tyr His Leu Met
                    85                  90                  95
Val Leu Pro Thr Phe Ile Arg Arg Phe Asn Arg Val Lys Met Gly
                100                 105                 110
Phe Phe Leu His Ser Pro Phe Pro Ser Ser Glu Ile Tyr Arg Thr Leu
                115                 120                 125
Pro Val Arg Glu Glu Ile Leu Lys Ala Leu Leu Asn Ser Asp Ile Ile
                130                 135                 140
Gly Phe His Thr Phe Asp Tyr Ala Arg His Phe Leu Ser Cys Cys Ser
145                 150                 155                 160
Arg Met Leu Gly Leu Glu Tyr Gln Ser Lys Arg Gly Tyr Leu Gly Leu
                165                 170                 175
Glu Tyr Tyr Gly Arg Thr Ile Ser Ile Lys Ile Met Pro Val Gly Ile
                180                 185                 190
His Met Gly Arg Ile Glu Ser Val Met Arg Met Ala Asp Glu Glu Cys
            195                 200                 205
Lys Val Arg Glu Leu Lys Gln Lys Phe Glu Gly Lys Thr Ile Leu Leu
            210                 215                 220
Gly Ile Asp Asp Met Asp Ile Phe Lys Gly Ile Asn Leu Lys Ile Leu
225                 230                 235                 240
Ala Met Glu Gln Met Leu Arg Gln His Pro Lys Trp Gln Gly Arg Ala
                245                 250                 255
Val Leu Val Gln Ile Val Asn Pro Ala Arg Gly Lys Gly Ile His Leu
                260                 265                 270
Glu Glu Ile His Ala Glu Ile Gln Glu Ser Cys Asn Arg Ile Asn Arg
            275                 280                 285
Val Phe Gly Arg Pro Gly Tyr Glu Pro Ile Val Phe Ile Asp Arg Ala
            290                 295                 300
Val Pro Ile Ala Glu Lys Val Ala Tyr Tyr Cys Ile Ala Glu Cys Val
305                 310                 315                 320
Ile Val Thr Ala Val Arg Asp Gly Met Asn Leu Thr Pro Tyr Glu Tyr
                325                 330                 335
Ile Ala Cys Arg Gln Gly Ile Ser Gly Ser Glu Ser Cys Ser Asn Val
            340                 345                 350
Asn Asp Pro Lys Lys Ser Met Leu Val Ile Ser Glu Phe Ile Gly Cys
            355                 360                 365
Ser Pro Ser Leu Ser Gly Ala Ile Arg Val Asn Pro Trp Asn Val Glu
            370                 375                 380
Ala Thr Ser Glu Ala Met Asn Glu Ala Ile Ser Thr Gly Asp Gly Glu
385                 390                 395                 400
Lys Gln Leu Arg His Glu Lys His Tyr Arg Tyr Val Ser Thr His Asp
                405                 410                 415
Val Ala Tyr Trp Ser Arg Ser Phe Leu Gln Asp Met Glu Arg Ala Cys
            420                 425                 430
Thr Asp Leu Leu Arg Lys Arg Cys Trp Gly Ile Gly Leu Ser Phe Gly
            435                 440                 445
```

Phe Arg Val Val Ala Leu Asp Pro Asn Phe Lys Lys Leu Ser Ile Asp
        450                 455                 460

Ala Met Val Ser Ala Tyr Lys Arg Ala Lys Asn Arg Ala Ile Leu Leu
465                 470                 475                 480

Asp Tyr Asp Gly Thr Val Met Pro Gln Asn Ser Ile Asn Lys Ser Pro
                485                 490                 495

Ser Lys Glu Val Leu Ser Ile Leu Glu Ser Leu Ser Glu Asp Pro Lys
            500                 505                 510

Asn Val Val Phe Ile Val Ser Gly Arg Gly Arg Asn Ser Leu Ser Asp
        515                 520                 525

Trp Phe Asn Ser Cys Glu Lys Leu Gly Ile Ala Ala Glu His Gly Tyr
    530                 535                 540

Phe Leu Arg Trp Ser His Asn Arg Glu Trp Glu Asn Cys Gly Lys Ser
545                 550                 555                 560

Ser Asp Phe Gly Trp Met Gln Ile Ala Glu Pro Val Met Lys Leu Tyr
                565                 570                 575

Thr Glu Ala Thr Asp Gly Ser Ser Ile Glu Arg Lys Glu Ser Ala Leu
            580                 585                 590

Val Trp Gln Tyr Arg Asp Ala Asp Leu Gly Phe Gly Ser Ala Gln Ala
        595                 600                 605

Lys Glu Met Leu Asp His Leu Glu Ser Val Leu Ala Asn Glu Pro Val
    610                 615                 620

Ala Val Lys Ser Gly Gln Phe Ile Val Glu Val Lys Pro Gln Asp Val
625                 630                 635                 640

Ser Lys Gly Leu Val Ala Glu Lys Ile Phe Ser Ser Met Asp Gly Lys
                645                 650                 655

Gly Lys Gln Ala Asp Phe Val Leu Cys Val Gly Asp Asp Arg Ser Asp
            660                 665                 670

Glu Asp Met Phe Glu Ile Val Ser Ser Ala Ile Ser Arg Asn Ile Leu
        675                 680                 685

Ala Thr Asn Ala Ser Val Phe Ala Cys Thr Val Gly Gln Lys Pro Ser
    690                 695                 700

Lys Ala Lys Tyr Tyr Leu Asp Asp Thr Thr Glu Val Thr Ser Met Leu
705                 710                 715                 720

Glu Ser Leu Ala Glu Glu Ser Asp Ala Ser Pro Tyr Ile Glu Glu Thr
                725                 730                 735

Gly Asp Ser Ser Arg Arg Gln Val
            740

<210> SEQ ID NO 13
<211> LENGTH: 2511
<212> TYPE: DNA
<213> ORGANISM: Triticum aestivum

<400> SEQUENCE: 13
gcacgagcaa gcactacatg tggccgctcc tccactacct gctcccgctc acgccctcca      60
cgctcggggg gctgcccttc gaccgcgcgc tctaccactc cttcctctcc gccaaccgcg     120
ccttcgccga ccgcctcacc gaggtgctcg ccccgacga cgacttcgtc tggatccagg      180
actaccacct cctcgccctc ccaccttcc tccgcaagcg cttcccgcgc gcagggtcg      240 gattcttcct ccactcgccc ttcccctcct ccgagatctt ccgcaccatc ccgtccgcg      300 acgacctgct ccgcgccctc ctcaacgccg acctcgtcgg cttccacacc ttcgactacg     360
cgcgccactt cctttcggcc tgctcccgcc tcctcggcct cgactaccag tccaagcgcg     420

-continued

```
gatacatcgg catcgagtac tacggccgca ccgtcaccgt caagattctg cccgtcggca    480
tcgacatggg ccagctccgg tcggtcgtgt cggcgccgga cacggcggac gtggtgcgcc    540
aggtcgccga cgcctacaag gggaggcgcc tcatgctcgg cgtggacgac gtcgacctct    600
tcaaggggat cgggctcaag ttcctgggga tggagcagct gctggtggag aaccccgagc    660
tccggggcaa ggccgtgctc gtgcaaatca ccaatccggc gcgcagcgag ggccgggacg    720
tgcaggaggt gcaggatgag gccagagcca tcagcgcccg tgtcaacgag cggttcggca    780
cccccgggta cacccccatc gtgatgatca gccgccggt gtcggagcac gagaaggcgg     840
cttactacgc cgccgccgag tgctgcgtgg tgagcgccgt ccgcgacggg ctcaaccgga    900
ttccgtacat ctacacggtg tgccggcagg agagcaccgc cctgggcgac gccccaagc    960 gaagcgtcat cgtgctgtcc gagttcgtgg gatgctcccc gtcgctcagc ggggcgatcc   1020
cgggtgaacc catggagcgt ggagtccgtg cagaggcca tgagctcggc attgaggatg    1080
tccgacggcg agcagcggct gcgccacgag aagcattaca agtatgtgag cacccatgat   1140
gtggcctact gggcgcggtc cttcgaccag gacctgcagc gggcctgcaa ggaccatttc   1200
tcgtggcggc attgggggat tgggttcggg atgagcttca aggtggtggc gcttggccca   1260
aatttcaggc ggctctccgt cgagcacatt gtgccgtcgt tcaggaagac ggagaaccgg   1320
ctgattctcc tggactacga tggcacggtg atgccggaga gttccatcga caaggcgccg   1380
agcagtgagg tcatctctgt cttgaatcgg ctgtgcgaag atccgaagaa cagggtgttc   1440
atcgtgagcg gtcgggggaa ggatgagctg agcaagtgg tcgcgccatg tgagaagctg    1500
ggaattgctg cagagcatgg ctacttcact aggtggagca aggaatcgcc atgggagacc   1560
tgcgggctgt tggcagactt cgattggaag aagacgccg agccggtgat gagactgtac    1620
acagaggcca ccgatggatc gtacatcgag cacaaggaga gcgcgctggt gtggcaccac   1680
gacgaggcgg atcctgactt cggttcatgc aggcgaagg agctgctcga ccatctcgag   1740
agcgtgctcg ccaacgagcc agtcgtcgtg aagagggcc agcacatcgt ggaggttaac    1800
ccccagggca tcagcaaggg cgtggtggtg gagagcctcc tgtcgtccat ggtgcgcggc   1860
ggcaaggcgc ccgacttcgt gctctgcatc ggggacgacc ggtccgacga ggacatgttc   1920
gagagcatcg tgtgcccggc caacggcagc gtgaagctcc cggcgacgag cgaggtgttc   1980
gcgtgcaccg tggggaagaa gccgagcatg gccaagtact acctggacga cacggtggac   2040
gtgatcaaga tgctgcaggg gctcgcgaac gcgccgtcgc agcagcggcc gtggcccgtg   2100
cagctccggg tcaccttcga ggaaggaaac ggagtatgaa caaaccaagg aggagatgtc   2160
aataaccagt gaaaaagaa ggacgacggt ggtgatgatg atgatgatga ttcagcgagt    2220
cggttggtgt ggtttagga ttagctgcag ttacaggata aacaggtttc tttcttcttc    2280
tttcttctgc ttcttttct ggtttacgtt tccgacctct tcctctcgcg cacgcatata    2340
catatgcccg cccgccccca tacattgagc gtgagaggga gaggtttgtt ccttcgggtc   2400
acattgtata tgtagttgac gatgacgatg aagatgaaat caatcagagc aagaaaatg    2460 attctttcaa aaaaaaaaaa aaaaaaaaaa aaaaaaaaaa aaaaaaaaa a             2511
```

<210> SEQ ID NO 14
<211> LENGTH: 378
<212> TYPE: PRT
<213> ORGANISM: Triticum aestivum

<400> SEQUENCE: 14

-continued

```
Thr Ser Lys His Tyr Met Trp Pro Leu Leu His Tyr Leu Leu Pro Leu
  1               5                  10                  15

Thr Pro Ser Thr Leu Gly Gly Leu Pro Phe Asp Arg Ala Leu Tyr His
             20                  25                  30

Ser Phe Leu Ser Ala Asn Arg Ala Phe Ala Asp Arg Leu Thr Glu Val
         35                  40                  45

Leu Ala Pro Asp Asp Asp Phe Val Trp Ile Gln Asp Tyr His Leu Leu
     50                  55                  60

Ala Leu Pro Thr Phe Leu Arg Lys Arg Phe Pro Arg Ala Arg Val Gly
 65                  70                  75                  80

Phe Phe Leu His Ser Pro Phe Pro Ser Ser Glu Ile Phe Arg Thr Ile
                 85                  90                  95

Pro Val Arg Asp Asp Leu Leu Arg Ala Leu Leu Asn Ala Asp Leu Val
            100                 105                 110

Gly Phe His Thr Phe Asp Tyr Ala Arg His Phe Leu Ser Ala Cys Ser
            115                 120                 125

Arg Leu Leu Gly Leu Asp Tyr Gln Ser Lys Arg Gly Tyr Ile Gly Ile
        130                 135                 140

Glu Tyr Tyr Gly Arg Thr Val Thr Val Lys Ile Leu Pro Val Gly Ile
145                 150                 155                 160

Asp Met Gly Gln Leu Arg Ser Val Val Ser Ala Pro Glu Thr Ala Asp
                165                 170                 175

Val Val Arg Gln Val Ala Asp Ala Tyr Lys Gly Arg Arg Leu Met Leu
            180                 185                 190

Gly Val Asp Asp Val Asp Leu Phe Lys Gly Ile Gly Leu Lys Phe Leu
        195                 200                 205

Gly Met Glu Gln Leu Leu Val Glu Asn Pro Glu Leu Arg Gly Lys Ala
    210                 215                 220

Val Leu Val Gln Ile Thr Asn Pro Ala Arg Ser Glu Gly Arg Asp Val
225                 230                 235                 240

Gln Glu Val Gln Asp Glu Ala Arg Ala Ile Ser Ala Arg Val Asn Glu
                245                 250                 255

Arg Phe Gly Thr Pro Gly Tyr Thr Pro Ile Val Met Ile Ser Arg Pro
            260                 265                 270

Val Ser Glu His Glu Lys Ala Ala Tyr Tyr Ala Ala Ala Glu Cys Cys
        275                 280                 285

Val Val Ser Ala Val Arg Asp Gly Leu Asn Arg Ile Pro Tyr Ile Tyr
    290                 295                 300

Thr Val Cys Arg Gln Glu Ser Thr Ala Leu Gly Asp Ala Pro Lys Arg
305                 310                 315                 320

Ser Val Ile Val Leu Ser Glu Phe Val Gly Cys Ser Pro Ser Leu Ser
                325                 330                 335

Gly Ala Ile Pro Gly Glu Pro Met Glu Arg Gly Val Arg Gly Arg Gly
            340                 345                 350

His Glu Leu Gly Ile Glu Asp Val Arg Arg Ala Ala Ala Ala Ala Pro
        355                 360                 365

Arg Glu Ala Leu Gln Val Cys Glu His Pro
    370                 375

<210> SEQ ID NO 15
<211> LENGTH: 1613
<212> TYPE: DNA
<213> ORGANISM: Zea mays
<220> FEATURE:
<221> NAME/KEY: CDS
```

<222> LOCATION: (232)..(1338)
<223> OTHER INFORMATION:

<400> SEQUENCE: 15

| | |
|---|---|
| ctctctcttc tctctctctc tctacggatt gcctcacacg catctcgcgt gcaattcaag | 60 |
| ttctcaggta ctccgccgtt gatgaactgc ctccacacct gcggcgacaa gaagacgctg | 120 |
| aagaagtggt ttttcatcga caagacagta ggctaaatcc agtcccagag aacaaattga | 180 |
| agcaccactc cccaccgcac agcagcacag ctcttctctt caccgatccc g atg gat | 237 |
|                                                                                                                                     Met Asp<br>                                                                                                                                       1 |
| atg ggc agc ggc tcg tca cct gtc atc acc gat ccg ata tcg ata agc<br>Met Gly Ser Gly Ser Ser Pro Val Ile Thr Asp Pro Ile Ser Ile Ser<br>           5                      10                       15 | 285 |
| cca ccg ctg ctg gga ggc ttg acg tcg aac ctg atg ccg ttc tcg gtc<br>Pro Pro Leu Leu Gly Gly Leu Thr Ser Asn Leu Met Pro Phe Ser Val<br>      20                      25                       30 | 333 |
| atg tcc gga ggc tgc tcc tcc agt cct agc atg agc gcc agc agc agg<br>Met Ser Gly Gly Cys Ser Ser Pro Ser Met Ser Ala Ser Ser Arg<br>35                    40                       45                     50 | 381 |
| cgt aaa atc gag gag gtc ctt gtc aat ggc ctg cta gac gcg atg aaa<br>Arg Lys Ile Glu Glu Val Leu Val Asn Gly Leu Leu Asp Ala Met Lys<br>               55                         60                     65 | 429 |
| tcg tcg tcg cct cgc aag aag cac aac ctc gcc ttc gga cag gat aat<br>Ser Ser Ser Pro Arg Lys Lys His Asn Leu Ala Phe Gly Gln Asp Asn<br>           70                      75                       80 | 477 |
| tcg ccc gac gaa gat cct gct tac act gca tgg ctg tca aaa tgc cct<br>Ser Pro Asp Glu Asp Pro Ala Tyr Thr Ala Trp Leu Ser Lys Cys Pro<br>85                    90                       95 | 525 |
| tct gcg ctg gcc tcc ttc aag cag ata gta gcc aac gca cag ggc agg<br>Ser Ala Leu Ala Ser Phe Lys Gln Ile Val Ala Asn Ala Gln Gly Arg<br>      100                     105                   110 | 573 |
| agg atc gct gtt ttc ttg gat tac gac ggc acc ctg tcg ccg atc gtc<br>Arg Ile Ala Val Phe Leu Asp Tyr Asp Gly Thr Leu Ser Pro Ile Val<br>115                  120                   125              130 | 621 |
| gac gat ccc gac aaa gcg ttc atg tcc cct gtg atg aga gct gct gtt<br>Asp Asp Pro Asp Lys Ala Phe Met Ser Pro Val Met Arg Ala Ala Val<br>               135                   140                   145 | 669 |
| aga aat gtc gcg aag tac ttc cct acc gcg att gtc agc gga agg tcc<br>Arg Asn Val Ala Lys Tyr Phe Pro Thr Ala Ile Val Ser Gly Arg Ser<br>           150                     155                   160 | 717 |
| cgt aag aag gtg ttt gaa ttt gta aaa ctg acg gaa ctg tac tac gct<br>Arg Lys Lys Val Phe Glu Phe Val Lys Leu Thr Glu Leu Tyr Tyr Ala<br>               165                   170                   175 | 765 |
| ggt agt cac ggg atg gac ata gtg aca tct gca gca gca cat gct act<br>Gly Ser His Gly Met Asp Ile Val Thr Ser Ala Ala Ala His Ala Thr<br>      180                     185                       190 | 813 |
| gaa aag tgc aaa gaa gcc aat ctc ttc caa cct gct tgc gag ttt ctc<br>Glu Lys Cys Lys Glu Ala Asn Leu Phe Gln Pro Ala Cys Glu Phe Leu<br>195                    200                   205              210 | 861 |
| cct atg att aat gag gtt tcc aag tgc ctc gtg gag gtc acg agt tca<br>Pro Met Ile Asn Glu Val Ser Lys Cys Leu Val Glu Val Thr Ser Ser<br>               215                   220                   225 | 909 |
| att gaa ggt gca aga gtt gag aac aac aag ttc tgt gta tct gta cat<br>Ile Glu Gly Ala Arg Val Glu Asn Asn Lys Phe Cys Val Ser Val His<br>          230                     235                   240 | 957 |
| tac cgc aac gta gca gag aag gac tgg aaa gtg gtc gca gga ctc gtg<br>Tyr Arg Asn Val Ala Glu Lys Asp Trp Lys Val Val Ala Gly Leu Val<br>               245                   250                   255 | 1005 |

```
aaa caa gtc ttg gag gcc ttc cct cgt ctc aaa gta acc aac ggg cga    1053
Lys Gln Val Leu Glu Ala Phe Pro Arg Leu Lys Val Thr Asn Gly Arg
    260             265                 270 atg gtt tta gag gtt cgc ccg gtg atc gac tgg gac aag gga aag gct    1101
Met Val Leu Glu Val Arg Pro Val Ile Asp Trp Asp Lys Gly Lys Ala
275                 280                 285                 290 gtc gag ttc ctg ctt cgg tcg ctc ggc cta agc gac tcc gaa gat gtg    1149
Val Glu Phe Leu Leu Arg Ser Leu Gly Leu Ser Asp Ser Glu Asp Val
                295                 300                 305 gtt cct atc tac atc gga gac gat cga aca gac gaa gac gcc ttc aag    1197
Val Pro Ile Tyr Ile Gly Asp Asp Arg Thr Asp Glu Asp Ala Phe Lys
            310                 315                 320 gta ctg cga gag cga agc tgt gga tac gga atc cta gtc tcg cag gtg    1245
Val Leu Arg Glu Arg Ser Cys Gly Tyr Gly Ile Leu Val Ser Gln Val
        325                 330                 335 ccc aag gac act gaa gcc ttc tac tcg gtg aga gac ccg tct gaa gtg    1293
Pro Lys Asp Thr Glu Ala Phe Tyr Ser Val Arg Asp Pro Ser Glu Val
340                 345                 350 atg ggg ttc ctc aat tcc ttg gtg aga tgg aag aag cac ccg ctg        1338
Met Gly Phe Leu Asn Ser Leu Val Arg Trp Lys Lys His Pro Leu
355                 360                 365 tgacgcaact gaaaacacaa cgactgattc agaagccgta aagcgactgt acttcgtgcg   1398
gcggcaattt tgtagagttt ttggctcacc gggtggctca ttctttcatg cgttttatt   1458 ttttattttt ttaactgtca cagtccttcg tcactgagaa ataacaagtg gttgtcccac   1518
accctcttgc aactgtaatc tgtaagcaag aggccctccc tgttcggtct atatatatat   1578
attgaataaa accgggacgc ttttgccttg ccctg                              1613

<210> SEQ ID NO 16
<211> LENGTH: 369
<212> TYPE: PRT
<213> ORGANISM: Zea mays

<400> SEQUENCE: 16

Met Asp Met Gly Ser Gly Ser Ser Pro Val Ile Thr Asp Pro Ile Ser
1               5                   10                  15

Ile Ser Pro Pro Leu Leu Gly Gly Leu Thr Ser Asn Leu Met Pro Phe
            20                  25                  30

Ser Val Met Ser Gly Gly Cys Ser Ser Pro Ser Met Ser Ala Ser
        35                  40                  45

Ser Arg Arg Lys Ile Glu Glu Val Leu Val Asn Gly Leu Leu Asp Ala
    50                  55                  60

Met Lys Ser Ser Ser Pro Arg Lys Lys His Asn Leu Ala Phe Gly Gln
65                  70                  75                  80

Asp Asn Ser Pro Asp Glu Asp Pro Ala Tyr Thr Ala Trp Leu Ser Lys
                85                  90                  95

Cys Pro Ser Ala Leu Ala Ser Phe Lys Gln Ile Val Ala Asn Ala Gln
            100                 105                 110

Gly Arg Arg Ile Ala Val Phe Leu Asp Tyr Asp Gly Thr Leu Ser Pro
        115                 120                 125

Ile Val Asp Asp Pro Asp Lys Ala Phe Met Ser Pro Val Met Arg Ala
    130                 135                 140

Ala Val Arg Asn Val Ala Lys Tyr Phe Pro Thr Ala Ile Val Ser Gly
145                 150                 155                 160

Arg Ser Arg Lys Lys Val Phe Glu Phe Val Lys Leu Thr Glu Leu Tyr
                165                 170                 175
```

-continued

```
Tyr Ala Gly Ser His Gly Met Asp Ile Val Thr Ser Ala Ala Ala His
            180                 185                 190

Ala Thr Glu Lys Cys Lys Glu Ala Asn Leu Phe Gln Pro Ala Cys Glu
        195                 200                 205

Phe Leu Pro Met Ile Asn Glu Val Ser Lys Cys Leu Val Glu Val Thr
        210                 215                 220

Ser Ser Ile Glu Gly Ala Arg Val Glu Asn Asn Lys Phe Cys Val Ser
225                 230                 235                 240

Val His Tyr Arg Asn Val Ala Glu Lys Asp Trp Lys Val Val Ala Gly
                245                 250                 255

Leu Val Lys Gln Val Leu Glu Ala Phe Pro Arg Leu Lys Val Thr Asn
            260                 265                 270

Gly Arg Met Val Leu Glu Val Arg Pro Val Ile Asp Trp Asp Lys Gly
        275                 280                 285

Lys Ala Val Glu Phe Leu Leu Arg Ser Leu Gly Leu Ser Asp Ser Glu
        290                 295                 300

Asp Val Val Pro Ile Tyr Ile Gly Asp Asp Arg Thr Asp Glu Asp Ala
305                 310                 315                 320

Phe Lys Val Leu Arg Glu Arg Ser Cys Gly Tyr Gly Ile Leu Val Ser
                325                 330                 335

Gln Val Pro Lys Asp Thr Glu Ala Phe Tyr Ser Val Arg Asp Pro Ser
            340                 345                 350

Glu Val Met Gly Phe Leu Asn Ser Leu Val Arg Trp Lys Lys His Pro
        355                 360                 365

Leu
```

<210> SEQ ID NO 17
<211> LENGTH: 1053
<212> TYPE: DNA
<213> ORGANISM: Oryza sativa
<220> FEATURE:
<221> NAME/KEY: CDS
<222> LOCATION: (2)..(643)
<223> OTHER INFORMATION:

<400> SEQUENCE: 17

```
t aca gcc tct tct tct tgg ggt gtt ctt gac tgg aag gtt tct ttg gtg      49
  Thr Ala Ser Ser Ser Trp Gly Val Leu Asp Trp Lys Val Ser Leu Val
  1               5                   10                  15 atg gcg aag gcg agc gag acg atg cgg atg gcc gtg cgc agc gtg gcg      97
Met Ala Lys Ala Ser Glu Thr Met Arg Met Ala Val Arg Ser Val Ala
            20                  25                  30 aag cac ttc ccg acg gcg atc gtg agc ggg cgg tgc cgc gac aag gtg     145
Lys His Phe Pro Thr Ala Ile Val Ser Gly Arg Cys Arg Asp Lys Val
        35                  40                  45 ttc gag ttc gtg aag ctc gcc gag ctg tac tac gcg ggg agc cac ggc     193
Phe Glu Phe Val Lys Leu Ala Glu Leu Tyr Tyr Ala Gly Ser His Gly
    50                  55                  60 atg gac atc aag ggc ccc gcc tcc cgc cac gcc gcc gcc aag tct cct     241
Met Asp Ile Lys Gly Pro Ala Ser Arg His Ala Ala Ala Lys Ser Pro
65                  70                  75                  80 ccc cac aac aag gga gtc ctc ttc cag ccg gcc agc gag ttc ctc ccc     289
Pro His Asn Lys Gly Val Leu Phe Gln Pro Ala Ser Glu Phe Leu Pro
                85                  90                  95 atg atc gag cag gtg cac cag cga ctc gag cag gcc acc agc tcc atc     337
Met Ile Glu Gln Val His Gln Arg Leu Glu Gln Ala Thr Ser Ser Ile
            100                 105                 110 ccg ggc gcc aag gtc gag aac aac aag ttc tgc gtc tcc gtc cac ttc     385
```

| | | | | | | | | | | | | | | | |
|---|---|---|---|---|---|---|---|---|---|---|---|---|---|---|---|
| Pro | Gly | Ala | Lys | Val | Glu | Asn | Asn | Lys | Phe | Cys | Val | Ser | Val | His | Phe |
| | | 115 | | | | 120 | | | | 125 | | | | | |

```
cgg tgc gtc gag ttc ctc ctc gac tcg ctc ggt ttc gcc gac tgc agc      433
Arg Cys Val Glu Phe Leu Leu Asp Ser Leu Gly Phe Ala Asp Cys Ser
    130                 135                 140 gac gtg ctg ccg gtc tac atc ggc gac gac cgc acg gac gag gac gcg      481
Asp Val Leu Pro Val Tyr Ile Gly Asp Asp Arg Thr Asp Glu Asp Ala
145                 150                 155                 160 ttc aag gtt ttg cgg cgg cgt ggg cag ggc gtg ggg atc ctg gtg tcc      529
Phe Lys Val Leu Arg Arg Arg Gly Gln Gly Val Gly Ile Leu Val Ser
                165                 170                 175 aag cac ccc aag gag acg agc gcc tcc ttc tcc ctc cag gag ccc gcc      577
Lys His Pro Lys Glu Thr Ser Ala Ser Phe Ser Leu Gln Glu Pro Ala
            180                 185                 190 gag gtg atg gag ttc ttg ctg cgg ctc gtg gag tgg aat cgc ctg tcc      625
Glu Val Met Glu Phe Leu Leu Arg Leu Val Glu Trp Asn Arg Leu Ser
        195                 200                 205 agg aca cgg ttg agg ctg taacaattga atttaaccgg cgaggctagc             673
Arg Thr Arg Leu Arg Leu
    210 tagagagaag cgcgtgatct gggccgtcca agcgattaca tcggcagggt aacccgtgac    733 gctgatcgat cgtggattct acaccaacac aggtgctcga aaatggtgtc cacattgcag    793 aagcgcagag agctaattaa tcaacgacgg acgagagaaa ctgatggctg tctggccatt    853 gttgtgccat aatcctgttt agttcttcac ctttctccct tcttctttt tcccatttgg    913 ggccccctt ttggtaccaa ccatgtaaat tccgtactac tagtaccttg tcatgcacaa    973 gaggaagatc aatgcaaata atgaagagca actaatgcaa gtatatactc atcaaaaaaa    1033 aaaaaaaaaa aaaaaaaaaa                                                1053

<210> SEQ ID NO 18
<211> LENGTH: 214
<212> TYPE: PRT
<213> ORGANISM: Oryza sativa

<400> SEQUENCE: 18
```

| | | | | | | | | | | | | | | | |
|---|---|---|---|---|---|---|---|---|---|---|---|---|---|---|---|
| Thr | Ala | Ser | Ser | Ser | Trp | Gly | Val | Leu | Asp | Trp | Lys | Val | Ser | Leu | Val |
| 1 | | | | 5 | | | | | 10 | | | | | 15 | |
| Met | Ala | Lys | Ala | Ser | Glu | Thr | Met | Arg | Met | Ala | Val | Arg | Ser | Val | Ala |
| | | | 20 | | | | | 25 | | | | | 30 | | |
| Lys | His | Phe | Pro | Thr | Ala | Ile | Val | Ser | Gly | Arg | Cys | Arg | Asp | Lys | Val |
| | | | 35 | | | | | 40 | | | | | 45 | | |
| Phe | Glu | Phe | Val | Lys | Leu | Ala | Glu | Leu | Tyr | Tyr | Ala | Gly | Ser | His | Gly |
| | 50 | | | | | 55 | | | | | 60 | | | | |
| Met | Asp | Ile | Lys | Gly | Pro | Ala | Ser | Arg | His | Ala | Ala | Lys | Ser | Pro | |
| 65 | | | | | 70 | | | | | 75 | | | | | 80 |
| Pro | His | Asn | Lys | Gly | Val | Leu | Phe | Gln | Pro | Ala | Ser | Glu | Phe | Leu | Pro |
| | | | | 85 | | | | | 90 | | | | | 95 | |
| Met | Ile | Glu | Gln | Val | His | Gln | Arg | Leu | Glu | Gln | Ala | Thr | Ser | Ser | Ile |
| | | | 100 | | | | | 105 | | | | | 110 | | |
| Pro | Gly | Ala | Lys | Val | Glu | Asn | Asn | Lys | Phe | Cys | Val | Ser | Val | His | Phe |
| | | | 115 | | | | | 120 | | | | | 125 | | |
| Arg | Cys | Val | Glu | Phe | Leu | Leu | Asp | Ser | Leu | Gly | Phe | Ala | Asp | Cys | Ser |
| | | 130 | | | | | 135 | | | | | 140 | | | |
| Asp | Val | Leu | Pro | Val | Tyr | Ile | Gly | Asp | Asp | Arg | Thr | Asp | Glu | Asp | Ala |
| 145 | | | | | 150 | | | | | 155 | | | | | 160 |

-continued

```
Phe Lys Val Leu Arg Arg Arg Gly Gln Gly Val Gly Ile Leu Val Ser
            165                 170                 175

Lys His Pro Lys Glu Thr Ser Ala Ser Phe Ser Leu Gln Glu Pro Ala
        180                 185                 190

Glu Val Met Glu Phe Leu Leu Arg Leu Val Glu Trp Asn Arg Leu Ser
    195                 200                 205

Arg Thr Arg Leu Arg Leu
    210

<210> SEQ ID NO 19
<211> LENGTH: 1904
<212> TYPE: DNA
<213> ORGANISM: Glycine max
<220> FEATURE:
<221> NAME/KEY: CDS
<222> LOCATION: (262)..(1407)
<223> OTHER INFORMATION:

<400> SEQUENCE: 19
gctttctctt ttcagttctc ttctcctctc tgcgcgacac agcacttcgt cactttcctt      60 ttttccatt  ctcatagcgt  ttttgtgttt  tcaagcaagc  gagtacggaa  ctcatctgtt    120
gataaactgc  tacctcaagc  agtgacaaga  aaagtggtgg  aagtttgata  gactttatag   180
ttcaatttgt  tctgaatact  ccttaaaaaa  aaggtcttac  attgttgctg  cactgtgaaa   240
ttgtgcatag acctggatcc a atg gac ctg aag cca aat ctt aac cct gtc         291
                        Met Asp Leu Lys Pro Asn Leu Asn Pro Val
                         1               5                   10 ctt act gat gcc aca ccc tta aca agg tca agg ctg ggt gtg cct tct         339
Leu Thr Asp Ala Thr Pro Leu Thr Arg Ser Arg Leu Gly Val Pro Ser
                15                  20                  25 ggt tta tca cct tac tct cct ata ggg gca acc ttt ccc cat ggt aac         387
Gly Leu Ser Pro Tyr Ser Pro Ile Gly Ala Thr Phe Pro His Gly Asn
         30                  35                  40 atg ctg gca att cca agg aag aag aca gga att ctt gac gat ttt cgt         435
Met Leu Ala Ile Pro Arg Lys Lys Thr Gly Ile Leu Asp Asp Phe Arg
     45                  50                  55 tct agc ggt tgg ctc gat gca atg aaa tcg tct tct cct act cac act         483
Ser Ser Gly Trp Leu Asp Ala Met Lys Ser Ser Ser Pro Thr His Thr
 60                  65                  70 aag gta tcc aag gat gtt agt cat ggg att gga tca cct gat tct gct         531
Lys Val Ser Lys Asp Val Ser His Gly Ile Gly Ser Pro Asp Ser Ala
 75                  80                  85                  90 tat agt acc tgg ctg cta aag ttt cca tca gca cta gca tct ttt gat         579
Tyr Ser Thr Trp Leu Leu Lys Phe Pro Ser Ala Leu Ala Ser Phe Asp
                 95                 100                 105 caa att acc aac tgt gca aaa ggg aag aga ata gca ttg ttt ctg gat         627
Gln Ile Thr Asn Cys Ala Lys Gly Lys Arg Ile Ala Leu Phe Leu Asp
            110                 115                 120 tat gat ggg act ctt tca ccc att gtg gat aat cct gac tct gct ttc         675
Tyr Asp Gly Thr Leu Ser Pro Ile Val Asp Asn Pro Asp Ser Ala Phe
        125                 130                 135 atg tca gac aat atg cgt gct gct gtt aaa ata gtg gcg gaa tat ttt         723
Met Ser Asp Asn Met Arg Ala Ala Val Lys Ile Val Ala Glu Tyr Phe
    140                 145                 150 cca acc gcg ata att agt gga aga agc cgt gac aag gta tat gaa ttt         771
Pro Thr Ala Ile Ile Ser Gly Arg Ser Arg Asp Lys Val Tyr Glu Phe
155                 160                 165                 170 gtt gga gta agt gat cta tgt tat gct ggt agt cat ggt atg gac att         819
Val Gly Val Ser Asp Leu Cys Tyr Ala Gly Ser His Gly Met Asp Ile
                175                 180                 185
```

```
att ggt cct tct aga caa tct att tct gat aat cac cct gat tgc att      867
Ile Gly Pro Ser Arg Gln Ser Ile Ser Asp Asn His Pro Asp Cys Ile
        190                 195                 200 agt tct gct gac aag cag ggt gtt gaa gtt aat tta ttc caa cct gct      915
Ser Ser Ala Asp Lys Gln Gly Val Glu Val Asn Leu Phe Gln Pro Ala
            205                 210                 215 gct gaa ttc ctg ccc atg att aat gag gta ctt ggg ttg ctc atg gag      963
Ala Glu Phe Leu Pro Met Ile Asn Glu Val Leu Gly Leu Leu Met Glu
220                 225                 230 tgc aca gaa gat att gaa gga gca aca gtt gag aac aac aaa ttt tgt     1011
Cys Thr Glu Asp Ile Glu Gly Ala Thr Val Glu Asn Asn Lys Phe Cys
235                 240                 245                 250 gtg tct gtg cat tac cgc aat gta gat gag gag agt tgg caa att gtg     1059
Val Ser Val His Tyr Arg Asn Val Asp Glu Glu Ser Trp Gln Ile Val
                255                 260                 265 gga caa cgt gta tat gat gtt ctg aag gag tat cca cgt ttg cgt tta     1107
Gly Gln Arg Val Tyr Asp Val Leu Lys Glu Tyr Pro Arg Leu Arg Leu
            270                 275                 280 act cat ggg cgg aag gtt tta gag gtt cgg cca gtg att gac tgg gat     1155
Thr His Gly Arg Lys Val Leu Glu Val Arg Pro Val Ile Asp Trp Asp
                285                 290                 295 aag gga aaa gct gtc aca ttt tta ctc gag tca ctt gga ctt aat tgt     1203
Lys Gly Lys Ala Val Thr Phe Leu Leu Glu Ser Leu Gly Leu Asn Cys
300                 305                 310 gat gac gtg ctc gct att tat gtt ggg gat gat aga aca gat gaa gat     1251
Asp Asp Val Leu Ala Ile Tyr Val Gly Asp Asp Arg Thr Asp Glu Asp
315                 320                 325                 330 gca ttt aag gtt ttg aaa gaa gct aat aaa ggt tgt ggc atc tta gtg     1299
Ala Phe Lys Val Leu Lys Glu Ala Asn Lys Gly Cys Gly Ile Leu Val
                335                 340                 345 tcc cgt gcc cca aaa gaa agc aac gca att tac tct ctt cgt gat ccc     1347
Ser Arg Ala Pro Lys Glu Ser Asn Ala Ile Tyr Ser Leu Arg Asp Pro
            350                 355                 360 tct gag gtc atg gaa ttt ctg aca tca ctt gcg gaa tgg aaa tca agc     1395
Ser Glu Val Met Glu Phe Leu Thr Ser Leu Ala Glu Trp Lys Ser Ser
                365                 370                 375 att caa gct cgc tgaaaagatt tacatattgt atagaggaga acatactcca         1447
Ile Gln Ala Arg
    380 ctatgctata tattagagac agtcttttgt ttttagtttg aatttttttgt tagaagactt  1507 tccaagaggt ctgctggaac atatttgagc tcagaagacc tctgacctga cgacagcaac  1567 aacattgtca ttacccaatt gttttactca aattttgtgt ggtagctgta aattcctggc  1627 tgagaattat atatatatat atatattggg aagattaagg aaaatctcct catagggtgt  1687 ttctttttc cgcattagaa gtttattatc gtattcattt catatccttt cttcagtttt   1747 ggttactgac cagctcattg gggattaaat atgaaactgt tctgtttctt tttttttgaga 1807 gaatatataa tttttaata tgtagattgg atatcattat ttgtattacc aatttatatc   1867 agtctgatta ccgttacata aaaaaaaaaa aaaaaaa                            1904

<210> SEQ ID NO 20
<211> LENGTH: 382
<212> TYPE: PRT
<213> ORGANISM: Glycine max

<400> SEQUENCE: 20

Met Asp Leu Lys Pro Asn Leu Asn Pro Val Leu Thr Asp Ala Thr Pro
1               5                   10                  15
```

```
Leu Thr Arg Ser Arg Leu Gly Val Pro Ser Gly Leu Ser Pro Tyr Ser
         20                  25                  30

Pro Ile Gly Ala Thr Phe Pro His Gly Asn Met Leu Ala Ile Pro Arg
         35                  40                  45

Lys Lys Thr Gly Ile Leu Asp Asp Phe Arg Ser Ser Gly Trp Leu Asp
 50                  55                  60

Ala Met Lys Ser Ser Pro Thr His Thr Lys Val Ser Lys Asp Val
 65                  70                  75                  80

Ser His Gly Ile Gly Ser Pro Asp Ser Ala Tyr Ser Thr Trp Leu Leu
                 85                  90                  95

Lys Phe Pro Ser Ala Leu Ala Ser Phe Asp Gln Ile Thr Asn Cys Ala
                 100                 105                 110

Lys Gly Lys Arg Ile Ala Leu Phe Leu Asp Tyr Asp Gly Thr Leu Ser
                 115                 120                 125

Pro Ile Val Asp Asn Pro Asp Ser Ala Phe Met Ser Asp Asn Met Arg
         130                 135                 140

Ala Ala Val Lys Ile Val Ala Glu Tyr Phe Pro Thr Ala Ile Ile Ser
145                 150                 155                 160

Gly Arg Ser Arg Asp Lys Val Tyr Glu Phe Val Gly Val Ser Asp Leu
                 165                 170                 175

Cys Tyr Ala Gly Ser His Gly Met Asp Ile Ile Gly Pro Ser Arg Gln
                 180                 185                 190

Ser Ile Ser Asp Asn His Pro Asp Cys Ile Ser Ser Ala Asp Lys Gln
                 195                 200                 205

Gly Val Glu Val Asn Leu Phe Gln Pro Ala Ala Glu Phe Leu Pro Met
         210                 215                 220

Ile Asn Glu Val Leu Gly Leu Leu Met Glu Cys Thr Glu Asp Ile Glu
225                 230                 235                 240

Gly Ala Thr Val Glu Asn Asn Lys Phe Cys Val Ser Val His Tyr Arg
                 245                 250                 255

Asn Val Asp Glu Glu Ser Trp Gln Ile Val Gly Gln Arg Val Tyr Asp
                 260                 265                 270

Val Leu Lys Glu Tyr Pro Arg Leu Arg Leu Thr His Gly Arg Lys Val
         275                 280                 285

Leu Glu Val Arg Pro Val Ile Asp Trp Asp Lys Gly Lys Ala Val Thr
         290                 295                 300

Phe Leu Leu Glu Ser Leu Gly Leu Asn Cys Asp Asp Val Leu Ala Ile
305                 310                 315                 320

Tyr Val Gly Asp Asp Arg Thr Asp Glu Asp Ala Phe Lys Val Leu Lys
                 325                 330                 335

Glu Ala Asn Lys Gly Cys Gly Ile Leu Val Ser Arg Ala Pro Lys Glu
                 340                 345                 350

Ser Asn Ala Ile Tyr Ser Leu Arg Asp Pro Ser Glu Val Met Glu Phe
         355                 360                 365

Leu Thr Ser Leu Ala Glu Trp Lys Ser Ser Ile Gln Ala Arg
         370                 375                 380

<210> SEQ ID NO 21
<211> LENGTH: 1383
<212> TYPE: DNA
<213> ORGANISM: Glycine max
<220> FEATURE:
<221> NAME/KEY: CDS
<222> LOCATION: (3)..(1091)
<223> OTHER INFORMATION:
```

<400> SEQUENCE: 21

```
cc ctt gtg gag ttg gca atg tcg att tca aac aca agt gct cta cct         47
   Leu Val Glu Leu Ala Met Ser Ile Ser Asn Thr Ser Ala Leu Pro
   1               5                   10                  15 aga gct acg gtg cct gga ata atg gcc ttg ctt ggt ggg gtt ttg ggc        95
Arg Ala Thr Val Pro Gly Ile Met Ala Leu Leu Gly Gly Val Leu Gly
                20                  25                  30 cta ccc cag aag aag ctc tta atg aaa act ttg gaa gat gga agt gtt       143
Leu Pro Gln Lys Lys Leu Leu Met Lys Thr Leu Glu Asp Gly Ser Val
            35                  40                  45 aat aaa gga ggg acc aaa gtt att aac aca tgg att gat tca atg aga       191
Asn Lys Gly Gly Thr Lys Val Ile Asn Thr Trp Ile Asp Ser Met Arg
        50                  55                  60 gcc tct tct ccc aca cga gtc aaa tcc aca caa aac caa gac cca aca       239
Ala Ser Ser Pro Thr Arg Val Lys Ser Thr Gln Asn Gln Asp Pro Thr
    65                  70                  75 agt cct tgg aca ctt tac cac cct tcg gca ctg agc atg ttt gat cag       287
Ser Pro Trp Thr Leu Tyr His Pro Ser Ala Leu Ser Met Phe Asp Gln
80                  85                  90                  95 att gta tgt gag tcc aaa gga aag cag att gtg act ttt ctt gac tat       335
Ile Val Cys Glu Ser Lys Gly Lys Gln Ile Val Thr Phe Leu Asp Tyr
                100                 105                 110 gat gga act ctc tcc cca att gtt gca gat cca gat aaa gca tac atg       383
Asp Gly Thr Leu Ser Pro Ile Val Ala Asp Pro Asp Lys Ala Tyr Met
            115                 120                 125 agt aaa aag atg agg acc aca ttg aag gac tta gca agg cat ttc ccc       431
Ser Lys Lys Met Arg Thr Thr Leu Lys Asp Leu Ala Arg His Phe Pro
        130                 135                 140 act gcc atc gtg agt gga agg tgc ctg gac aag gtg tat aac ttt gta       479
Thr Ala Ile Val Ser Gly Arg Cys Leu Asp Lys Val Tyr Asn Phe Val
    145                 150                 155 aga ttg gca gaa ctg tac tat gct ggg agc cat gga atg gac atc aag       527
Arg Leu Ala Glu Leu Tyr Tyr Ala Gly Ser His Gly Met Asp Ile Lys
160                 165                 170                 175 gga cca aca aat aag cga agt act aag aag gaa aat gaa caa gtg ctc       575
Gly Pro Thr Asn Lys Arg Ser Thr Lys Lys Glu Asn Glu Gln Val Leu
                180                 185                 190 ttc caa ccc gct agt gaa ttc ttg ccc atg atc aat gag gtg tac aac       623
Phe Gln Pro Ala Ser Glu Phe Leu Pro Met Ile Asn Glu Val Tyr Asn
            195                 200                 205 atc ttg gtg gaa aaa aca aag tct gtc cct ggg gct aag gta gaa aat       671
Ile Leu Val Glu Lys Thr Lys Ser Val Pro Gly Ala Lys Val Glu Asn
        210                 215                 220 aac aag ttt tgc ttg tcc gtg cac ttt cgc tgt gtt gac gaa aag agt       719
Asn Lys Phe Cys Leu Ser Val His Phe Arg Cys Val Asp Glu Lys Ser
    225                 230                 235 tgg gtg tca ttg gct gaa caa gtg agc ttc gtg ctc aac gag tac cca       767
Trp Val Ser Leu Ala Glu Gln Val Ser Phe Val Leu Asn Glu Tyr Pro
240                 245                 250                 255 aaa ctt aag cta act caa ggg aga aaa gtg ctt gag att cga cca acc       815
Lys Leu Lys Leu Thr Gln Gly Arg Lys Val Leu Glu Ile Arg Pro Thr
                260                 265                 270 ata aaa tgg gac aag ggc aag gct ctt gaa ttc ttg cta gag tca ctg       863
Ile Lys Trp Asp Lys Gly Lys Ala Leu Glu Phe Leu Leu Glu Ser Leu
            275                 280                 285 gga tat gct aat tct gat aat gta ttt cca atc tat att ggg gat gat       911
Gly Tyr Ala Asn Ser Asp Asn Val Phe Pro Ile Tyr Ile Gly Asp Asp
        290                 295                 300
```

```
cga act gat gaa gat gct ttt aag gtt tta cgg agg agg ggt cat ggg      959
Arg Thr Asp Glu Asp Ala Phe Lys Val Leu Arg Arg Arg Gly His Gly
    305                 310                 315 gtt ggg att cta gtt tct aaa att cca aaa gaa act gat gct tcc tac     1007
Val Gly Ile Leu Val Ser Lys Ile Pro Lys Glu Thr Asp Ala Ser Tyr
320                 325                 330                 335 act ttg caa gat cca aca gag gtt ggg cag ttt ttg agg cat ttg gtg     1055
Thr Leu Gln Asp Pro Thr Glu Val Gly Gln Phe Leu Arg His Leu Val
                340                 345                 350 gag tgg aaa aga acg agt tcc caa tac cac aag ttg tagattctta          1101
Glu Trp Lys Arg Thr Ser Ser Gln Tyr His Lys Leu
                355                 360 gatgaattca gggaaattga caccagccca taatttggtc aaggggtggt tccaattata   1161 tccctttct tgttcgaaat aggaaatagt gtgttccata atttaaagtt ttagggagga    1221
acaaagttga aatagctagc taggttctct ctctattttc ttttctaat gtaatctatt    1281 ccatcacacg tttgcatgcg catgcggata gtgaaagaat tgatgtttta tgccgcaatt   1341
gcgagtggcg cgtcaaaaaa aaaaaaaaaa aaaaaaaaa aa                       1383

<210> SEQ ID NO 22
<211> LENGTH: 363
<212> TYPE: PRT
<213> ORGANISM: Glycine max

<400> SEQUENCE: 22

Leu Val Glu Leu Ala Met Ser Ile Ser Asn Thr Ser Ala Leu Pro Arg
1               5                   10                  15

Ala Thr Val Pro Gly Ile Met Ala Leu Leu Gly Gly Val Leu Gly Leu
            20                  25                  30

Pro Gln Lys Lys Leu Leu Met Lys Thr Leu Glu Asp Gly Ser Val Asn
        35                  40                  45

Lys Gly Gly Thr Lys Val Ile Asn Thr Trp Ile Asp Ser Met Arg Ala
    50                  55                  60

Ser Ser Pro Thr Arg Val Lys Ser Thr Gln Asn Gln Asp Pro Thr Ser
65                  70                  75                  80

Pro Trp Thr Leu Tyr His Pro Ser Ala Leu Ser Met Phe Asp Gln Ile
                85                  90                  95

Val Cys Glu Ser Lys Gly Lys Gln Ile Val Thr Phe Leu Asp Tyr Asp
            100                 105                 110

Gly Thr Leu Ser Pro Ile Val Ala Asp Pro Asp Lys Ala Tyr Met Ser
        115                 120                 125

Lys Lys Met Arg Thr Thr Leu Lys Asp Leu Ala Arg His Phe Pro Thr
    130                 135                 140

Ala Ile Val Ser Gly Arg Cys Leu Asp Lys Val Tyr Asn Phe Val Arg
145                 150                 155                 160

Leu Ala Glu Leu Tyr Tyr Ala Gly Ser His Gly Met Asp Ile Lys Gly
                165                 170                 175

Pro Thr Asn Lys Arg Ser Thr Lys Lys Glu Asn Glu Gln Val Leu Phe
            180                 185                 190

Gln Pro Ala Ser Glu Phe Leu Pro Met Ile Asn Glu Val Tyr Asn Ile
        195                 200                 205

Leu Val Glu Lys Thr Lys Ser Val Pro Gly Ala Lys Val Glu Asn Asn
    210                 215                 220

Lys Phe Cys Leu Ser Val His Phe Arg Cys Val Asp Glu Lys Ser Trp
225                 230                 235                 240
```

-continued

```
Val Ser Leu Ala Glu Gln Val Ser Phe Val Leu Asn Glu Tyr Pro Lys
                245                 250                 255

Leu Lys Leu Thr Gln Gly Arg Lys Val Leu Glu Ile Arg Pro Thr Ile
            260                 265                 270

Lys Trp Asp Lys Gly Lys Ala Leu Glu Phe Leu Leu Glu Ser Leu Gly
        275                 280                 285

Tyr Ala Asn Ser Asp Asn Val Phe Pro Ile Tyr Ile Gly Asp Asp Arg
    290                 295                 300

Thr Asp Glu Asp Ala Phe Lys Val Leu Arg Arg Gly His Gly Val
305                 310                 315                 320

Gly Ile Leu Val Ser Lys Ile Pro Lys Glu Thr Asp Ala Ser Tyr Thr
                325                 330                 335

Leu Gln Asp Pro Thr Glu Val Gly Gln Phe Leu Arg His Leu Val Glu
            340                 345                 350

Trp Lys Arg Thr Ser Ser Gln Tyr His Lys Leu
        355                 360

<210> SEQ ID NO 23
<211> LENGTH: 924
<212> TYPE: DNA
<213> ORGANISM: Triticum aestivum
<220> FEATURE:
<221> NAME/KEY: CDS
<222> LOCATION: (2)..(679)
<223> OTHER INFORMATION:

<400> SEQUENCE: 23 g aga aac gtc gcc aag tac ttc cct gct gcc atc gtc agc gga agg tcc        49
  Arg Asn Val Ala Lys Tyr Phe Pro Ala Ala Ile Val Ser Gly Arg Ser
   1               5                  10                  15 cgg aag aag gtt ctt gaa ttc gta aaa ctg aag gaa ctc tgc tat gct        97
Arg Lys Lys Val Leu Glu Phe Val Lys Leu Lys Glu Leu Cys Tyr Ala
                20                  25                  30 ggt agt cat ggg atg gac ata atg aca tct tct tca gca cat tat gaa       145
Gly Ser His Gly Met Asp Ile Met Thr Ser Ser Ser Ala His Tyr Glu
            35                  40                  45 cgc aat gct gaa aag ggc aaa gaa gcc aac ctc ttc caa cct gct cgc       193
Arg Asn Ala Glu Lys Gly Lys Glu Ala Asn Leu Phe Gln Pro Ala Arg
        50                  55                  60 gat ttt ctg cct atg atc gat gag gtt tcc aag gtc ctc ttg gaa gtc       241
Asp Phe Leu Pro Met Ile Asp Glu Val Ser Lys Val Leu Leu Glu Val
65                  70                  75                  80 acg agc cga atc gaa ggc gca agc gtt gag gac aac aag ttc tgc gtg       289
Thr Ser Arg Ile Glu Gly Ala Ser Val Glu Asp Asn Lys Phe Cys Val
                85                  90                  95 tct gta cat tac cgc aac gtg gac gag aag gac tgg gag ctg gtc gca       337
Ser Val His Tyr Arg Asn Val Asp Glu Lys Asp Trp Glu Leu Val Ala
                100                 105                 110 cgg ctc gta aac gaa gtg ctg gag gac ttc ccc cgt ctc aaa gtg acc       385
Arg Leu Val Asn Glu Val Leu Glu Asp Phe Pro Arg Leu Lys Val Thr
            115                 120                 125 aac gga cga atg gtt tta gag gtt cgt cca gtg atc gac tgg gac aag       433
Asn Gly Arg Met Val Leu Glu Val Arg Pro Val Ile Asp Trp Asp Lys
        130                 135                 140 ggg aag gcc gtc gag ttc ctg ctt cag tcg ctc ggg ctg agc gac tcc       481
Gly Lys Ala Val Glu Phe Leu Leu Gln Ser Leu Gly Leu Ser Asp Ser
145                 150                 155                 160 gag aaa gtg atc cct atc tac atc ggc gac gac cgc acc gac gaa gac       529
Glu Lys Val Ile Pro Ile Tyr Ile Gly Asp Asp Arg Thr Asp Glu Asp
                165                 170                 175
```

```
gcg ttc aag gtg ctt cgg gag agg aac tgc gga tac ggg ata ctg gtc    577
Ala Phe Lys Val Leu Arg Glu Arg Asn Cys Gly Tyr Gly Ile Leu Val
        180                 185                 190 tcg cag gcg ccc aag gaa acc gag gcc ttc tac tcg ctc agg gac ccg    625
Ser Gln Ala Pro Lys Glu Thr Glu Ala Phe Tyr Ser Leu Arg Asp Pro
        195                 200                 205 tct gaa gtg atg gag ttc ctg aac tcc ttg gtg aga tgg aag aag cac    673
Ser Glu Val Met Glu Phe Leu Asn Ser Leu Val Arg Trp Lys Lys His
        210                 215                 220 tcg cta tgaacaaaca ggagatgact gtagtttccg aggcgacagt tttgcagcgt     729
Ser Leu
225 tggaaaccat agctagggtc gaatgatgtt gccgtcccct gttaattcgt ttaggtcgat   789 tgatattctt gtactgctag tcatgttctt tgccactgag aaatttgatc ggtggctgtg   849 ttggttgtta tacataatgc tttaggttaa caaaaaaaaa aaaaaaaaaa aaaaaaaaaa   909 aaaaaaaaaa aaaaa                                                   924

<210> SEQ ID NO 24
<211> LENGTH: 226
<212> TYPE: PRT
<213> ORGANISM: Triticum aestivum

<400> SEQUENCE: 24

Arg Asn Val Ala Lys Tyr Phe Pro Ala Ala Ile Val Ser Gly Arg Ser
1               5                   10                  15

Arg Lys Lys Val Leu Glu Phe Val Lys Leu Lys Glu Leu Cys Tyr Ala
            20                  25                  30

Gly Ser His Gly Met Asp Ile Met Thr Ser Ser Ala His Tyr Glu
        35                  40                  45

Arg Asn Ala Glu Lys Gly Lys Glu Ala Asn Leu Phe Gln Pro Ala Arg
    50                  55                  60

Asp Phe Leu Pro Met Ile Asp Glu Val Ser Lys Val Leu Leu Glu Val
65                  70                  75                  80

Thr Ser Arg Ile Glu Gly Ala Ser Val Glu Asp Asn Lys Phe Cys Val
                85                  90                  95

Ser Val His Tyr Arg Asn Val Asp Glu Lys Asp Trp Glu Leu Val Ala
            100                 105                 110

Arg Leu Val Asn Glu Val Leu Glu Asp Phe Pro Arg Leu Lys Val Thr
        115                 120                 125

Asn Gly Arg Met Val Leu Glu Val Arg Pro Val Ile Asp Trp Asp Lys
    130                 135                 140

Gly Lys Ala Val Glu Phe Leu Leu Gln Ser Leu Gly Leu Ser Asp Ser
145                 150                 155                 160

Glu Lys Val Ile Pro Ile Tyr Ile Gly Asp Asp Arg Thr Asp Glu Asp
                165                 170                 175

Ala Phe Lys Val Leu Arg Glu Arg Asn Cys Gly Tyr Gly Ile Leu Val
            180                 185                 190

Ser Gln Ala Pro Lys Glu Thr Glu Ala Phe Tyr Ser Leu Arg Asp Pro
        195                 200                 205

Ser Glu Val Met Glu Phe Leu Asn Ser Leu Val Arg Trp Lys Lys His
    210                 215                 220

Ser Leu
225
```

```
<210> SEQ ID NO 25
<211> LENGTH: 529
<212> TYPE: DNA
<213> ORGANISM: Glycine max
<220> FEATURE:
<221> NAME/KEY: unsure
<222> LOCATION: (493)
<223> OTHER INFORMATION: n is a, c, g or t
<220> FEATURE:
<221> NAME/KEY: unsure
<222> LOCATION: (507)
<223> OTHER INFORMATION: n is a, c, g or t

<400> SEQUENCE: 25
cctcaactcg ttattgtaca agtacgagtc ggatatttac actgccatcg agcaagtctt      60
tgggggtgaa ctcgaaatgg acgaagagtt tgaactctcg ccatggccca tcactgctga    120
ggctttcgcc gagggtgctg cacgtgaact ctcgacatcc cgcgttcaaa cggcggccga    180
gtggaaggaa cgcatggata agcgtcgtga tacgatgaat gagctctgct ggaatgaggg    240
acgaggaatg ttctttgact gggataccaa ggcgcagaaa caggccaaat acgagagtgt    300
tacctgtctc tggccactct gggctggaaa tgcgtccgag gatcaggcaa tgaagatggt    360
caatatggct ctacccaagt ttgaggtcgc tggcgggctt gtttcgggaa cagaggagag    420
ccgaggtatc atctcgatcg atcgaccgaa tcgacagtgg gattaacctt tcaagctggc    480
cgccgcatca gantatgact tgggtcnggc ttgacgatac ggcacgata               529

<210> SEQ ID NO 26
<211> LENGTH: 30
<212> TYPE: PRT
<213> ORGANISM: Glycine max

<400> SEQUENCE: 26

Leu Asn Ser Leu Leu Tyr Lys Tyr Glu Ser Asp Ile Tyr Thr Ala Ile
 1               5                  10                  15

Glu Gln Val Phe Gly Gly Glu Leu Glu Met Asp Glu Glu Phe
             20                  25                  30

<210> SEQ ID NO 27
<211> LENGTH: 461
<212> TYPE: DNA
<213> ORGANISM: Triticum aestivum
<220> FEATURE:
<221> NAME/KEY: unsure
<222> LOCATION: (432)
<223> OTHER INFORMATION: n is a, c, g or t
<220> FEATURE:
<221> NAME/KEY: unsure
<222> LOCATION: (461)
<223> OTHER INFORMATION: n is a, c, g or t

<400> SEQUENCE: 27
caagcactac atgtggccgc tcctccacta cctgctcccg ctcacgccct ccacgctcgg      60
ggggctgccc ttcgaccgcg cgctctacca ctccttcctc tccgccaacc gcgccttcgc    120
cgaccgcctc accgaggtgc tcgccccega cgacgacttc gtctggatcc aggactacca    180
cctcctcgcc ctcccacct tcctccgcaa gcgcttcccg cgcgccaggg tcggattctt    240
cctccactcg cccttcccct cctccgagat cttccgcacc atcccccgtcc gcgacgacct    300 gctccgcgcc ctcctcaacg ccgacctcgt cggcttccac accttcgact acgcgcgcca    360
cttcctttcg gctgctcccg cctcctcggc tcgactacag tcaaagcgcg gataatcggc    420
atcgagtata anggcgcacg tcaacgtcaa gattctgccg n                       461
```

<210> SEQ ID NO 28
<211> LENGTH: 120
<212> TYPE: PRT
<213> ORGANISM: Triticum aestivum

<400> SEQUENCE: 28

Met Trp Pro Leu Leu His Tyr Leu Leu Pro Leu Thr Pro Ser Thr Leu
 1               5                  10                  15

Gly Gly Leu Pro Phe Asp Arg Ala Leu Tyr His Ser Phe Leu Ser Ala
            20                  25                  30

Asn Arg Ala Phe Ala Asp Arg Leu Thr Glu Leu Ala Pro Asp Asp Asp
        35                  40                  45

Phe Val Trp Ile Gln Asp Tyr His Leu Leu Ala Leu Pro Thr Phe Leu
    50                  55                  60

Arg Lys Arg Phe Pro Arg Ala Arg Val Gly Phe Phe Leu His Ser Pro
65                  70                  75                  80

Phe Pro Ser Ser Glu Ile Phe Arg Thr Ile Pro Val Arg Asp Asp Leu
                85                  90                  95

Leu Arg Ala Leu Leu Asn Ala Asp Leu Val Gly Phe His Thr Phe Asp
            100                 105                 110

Tyr Ala Arg His Phe Leu Ser Ala
        115                 120

<210> SEQ ID NO 29
<211> LENGTH: 447
<212> TYPE: DNA
<213> ORGANISM: Oryza sativa

<400> SEQUENCE: 29
tacagcctct tcttcttggg gtgttcttga ctggaaggtt tctttggtga tggcgaaggc     60
gagcgagacg atgcggatgg ccgtgcgcag cgtggcgaag cacttcccga cggcgatcgt    120
gagcgggcgg tgccgcgaca aggtgttcga gttcgtgaag ctcgccgagc tgtactacgc    180
ggggagccac ggcatggaca tcaagggccc cgcctcccgc cacgccgccg ccaagtctcc    240
tccccacaac aagggagtcc tcttccagcc ggccagcgag ttcctcccca tgatcgagca    300
ggtgcaccaa gcgactcgag caggcaccaa gctccatccc gggcgccaag tcgaaacaa    360 caattctgcg tctccgtcca cttccggtgc gtcgattcct cctcgactcg ctcggtttcg    420
ccgactgcag cgactgctgc cggtcta                                        447

<210> SEQ ID NO 30
<211> LENGTH: 54
<212> TYPE: PRT
<213> ORGANISM: Oryza sativa

<400> SEQUENCE: 30

Ala Lys Ala Ser Glu Thr Met Arg Met Ala Val Arg Ser Val Ala Lys
 1               5                  10                  15

His Phe Pro Thr Ala Ile Val Ser Gly Arg Cys Arg Asp Lys Val Phe
            20                  25                  30

Glu Phe Val Lys Leu Ala Glu Leu Tyr Tyr Ala Gly Ser His Gly Met
        35                  40                  45

Asp Ile Lys Gly Pro Ala
        50

<210> SEQ ID NO 31
<211> LENGTH: 492

```
<212> TYPE: DNA
<213> ORGANISM: Glycine max
<220> FEATURE:
<221> NAME/KEY: unsure
<222> LOCATION: (384)
<223> OTHER INFORMATION: n is a, c, g or t
<220> FEATURE:
<221> NAME/KEY: unsure
<222> LOCATION: (435)
<223> OTHER INFORMATION: n is a, c, g or t
<220> FEATURE:
<221> NAME/KEY: unsure
<222> LOCATION: (488)
<223> OTHER INFORMATION: n is a, c, g or t

<400> SEQUENCE: 31
gctttctctt ttcagttctc ttctcctctc tgcgcgacac agcacttcgt cactttcctt      60
tttttccatt ctcatagcgt ttttgtgttt tcaagcaagc gagtacggaa ctcatctgtt     120
gataaactgc tacctcaagc agtgacaaga aaagtggtgg aagtttgata gactttatag     180
ttcaatttgt tctgaatact ccttaaaaaa aaggtcttac attgttgctg cactgtgaaa     240
ttgtgcatag acctggatcc aatggacctg aagccaaatc ttaaccctgt ccttactgat     300
gccacaccct taacaaggtc aaggctgggt gtgccttctg gtttatcacc ttactctcct     360
ataggggcaa cctttccccca tggnaacatg ctggcaattc caaggaagaa gacaggaatt     420
cttgacgatt ttcgntctag cggttggctc gatgcaatga aatcgtcttc tcctactcac     480
actaaggnat cc                                                         492

<210> SEQ ID NO 32
<211> LENGTH: 30
<212> TYPE: PRT
<213> ORGANISM: Glycine max

<400> SEQUENCE: 32

Asn Pro Val Leu Thr Asp Ala Thr Pro Leu Thr Arg Ser Arg Leu Gly
  1               5                  10                  15

Val Pro Ser Gly Leu Ser Pro Tyr Ser Pro Ile Gly Ala Thr
             20                  25                  30

<210> SEQ ID NO 33
<211> LENGTH: 541
<212> TYPE: DNA
<213> ORGANISM: Glycine max
<220> FEATURE:
<221> NAME/KEY: unsure
<222> LOCATION: (415)
<223> OTHER INFORMATION: n is a, c, g or t
<220> FEATURE:
<221> NAME/KEY: unsure
<222> LOCATION: (453)
<223> OTHER INFORMATION: n is a, c, g or t
<220> FEATURE:
<221> NAME/KEY: unsure
<222> LOCATION: (469)
<223> OTHER INFORMATION: n is a, c, g or t
<220> FEATURE:
<221> NAME/KEY: unsure
<222> LOCATION: (520)
<223> OTHER INFORMATION: n is a, c, g or t

<400> SEQUENCE: 33
cccttgtgga gttggcaatg tcgatttcaa acacaagtgc tctacctaga gctacggtgc      60
ctggaataat ggccttgctt ggtgggggttt tgggcctacc ccagaagaag ctcttaatga    120
aaactttgga agatggaagt gttaataaag gagggaccaa agttattaac acatggattg    180
```

| | | |
|---|---|---|
| attcaatgag agcctcttct cccacacgag tcaaatccac acaaaaccaa gacccaacaa | 240 |
| gtccttggac actttaccac ccttcggcac tgagcatgtt tgatcagatt gtatgtgagt | 300 |
| ccaaaggaaa gcagattgtg acttttcttg actatgatgg aactctctcc ccaattgttg | 360 |
| cagatccaag ataaagcata catgagtaaa aagatgagga ccacattgaa ggacntagca | 420 |
| aggcatttcc ccactgccaa ccgtgagtgg aangtgcctg gacaaggng tataactttg | 480 |
| gaaagattgg caaaactgta ctaagctggg agccatgggn atgggcatca agggaacaac | 540 |
| a | 541 |

<210> SEQ ID NO 34
<211> LENGTH: 90
<212> TYPE: PRT
<213> ORGANISM: Glycine max

<400> SEQUENCE: 34

Pro Gln Lys Lys Leu Leu Met Lys Thr Leu Glu Asp Gly Ser Val Asn
1               5                   10                  15

Lys Gly Gly Thr Lys Val Ile Asn Thr Trp Ile Asp Ser Met Arg Ala
            20                  25                  30

Ser Ser Pro Thr Arg Val Lys Ser Thr Gln Asn Gln Asp Pro Thr Ser
        35                  40                  45

Pro Trp Thr Leu Tyr His Pro Ser Ala Leu Ser Met Phe Asp Gln Ile
    50                  55                  60

Val Cys Glu Ser Lys Gly Lys Gln Ile Val Thr Phe Leu Asp Tyr Asp
65                  70                  75                  80

Gly Thr Leu Ser Pro Ile Val Ala Asp Pro
                85                  90

<210> SEQ ID NO 35
<211> LENGTH: 516
<212> TYPE: DNA
<213> ORGANISM: Triticum aestivum
<220> FEATURE:
<221> NAME/KEY: unsure
<222> LOCATION: (407)
<223> OTHER INFORMATION: n is a, c, g or t
<220> FEATURE:
<221> NAME/KEY: unsure
<222> LOCATION: (452)
<223> OTHER INFORMATION: n is a, c, g or t
<220> FEATURE:
<221> NAME/KEY: unsure
<222> LOCATION: (471)
<223> OTHER INFORMATION: n is a, c, g or t
<220> FEATURE:
<221> NAME/KEY: unsure
<222> LOCATION: (478)
<223> OTHER INFORMATION: n is a, c, g or t
<220> FEATURE:
<221> NAME/KEY: unsure
<222> LOCATION: (493)
<223> OTHER INFORMATION: n is a, c, g or t
<220> FEATURE:
<221> NAME/KEY: unsure
<222> LOCATION: (502)
<223> OTHER INFORMATION: n is a, c, g or t

<400> SEQUENCE: 35

| | | |
|---|---|---|
| gagaaacgtc gccaagtact tccctgctgc catcgtcagc ggaaggtccc ggaagaaggt | 60 |
| tcttgaattc gtaaaactga aggaactctg ctatgctggt agtcatggga tggacataat | 120 |
| gacatcttct tcagcacatt atgaacgcaa tgctgaaaag gcaaagaag ccaacctctt | 180 |
| ccaacctgct cgcgattttc tgcctatgat cgatgaggtt ccaaggtcc tcttggaagt | 240 |

```
cacgagccga atcgaaggcg caagcgttga ggacaacaag ttctgcgtgt ctgtacatta    300
ccgcaacgtg gacgagaagg actggggagc tggtcccacg gctcgtaaac gaatgctgga    360
ggacttcccc gtctcaaagt gaccaacgga cgaatggttt taaaagntcg tcaagtgatt    420
gactgggaca aggggaaggc cttcaatttc cngcttaatc ccccgggct naccaacncc     480 gagaaaagtg atncctatcc anatcgggga cgaccg                              516
```

<210> SEQ ID NO 36
<211> LENGTH: 41
<212> TYPE: PRT
<213> ORGANISM: Triticum aestivum

<400> SEQUENCE: 36

```
Arg Asn Val Ala Lys Tyr Phe Pro Ala Ala Ile Val Ser Gly Arg Ser
 1               5                  10                  15
Arg Lys Lys Val Leu Glu Phe Val Lys Leu Lys Glu Leu Cys Tyr Ala
                20                  25                  30
Gly Ser His Gly Met Asp Ile Met Thr
            35                  40
```

<210> SEQ ID NO 37
<211> LENGTH: 385
<212> TYPE: PRT
<213> ORGANISM: Arabidopsis thaliana

<400> SEQUENCE: 37

```
Met Asp Met Lys Ser Gly His Ser Ser Pro Val Met Thr Asp Ser Pro
 1               5                  10                  15
Pro Ile Ser Asn Ser Arg Leu Thr Ile Arg Gln Asn Arg Leu Pro Tyr
                20                  25                  30
Ser Ser Ala Ala Ala Thr Ala Ile Ser Gln Asn Asn Asn Leu Leu Leu
            35                  40                  45
Thr Val Pro Arg Lys Lys Thr Gly Ile Leu Asp Asp Val Lys Ser Asn
        50                  55                  60
Gly Trp Leu Asp Ala Met Lys Ser Ser Ser Pro Pro Thr Ile Leu
 65                  70                  75                  80
Asn Lys Asp Asn Leu Ser Asn Asp Ala Thr Asp Met Thr Tyr Arg Glu
                85                  90                  95
Trp Met Gln Leu Lys Tyr Pro Ser Ala Leu Thr Ser Phe Glu Lys Ile
                100                 105                 110
Met Ser Phe Ala Lys Gly Lys Arg Ile Ala Leu Phe Leu Asp Tyr Asp
            115                 120                 125
Gly Thr Leu Ser Pro Ile Val Glu Glu Pro Asp Cys Ala Tyr Met Ser
        130                 135                 140
Ser Ala Met Arg Ser Ala Val Gln Asn Val Ala Lys Tyr Phe Pro Thr
145                 150                 155                 160
Ala Ile Ile Ser Gly Arg Ser Arg Asp Lys Val Tyr Glu Phe Val Asn
                165                 170                 175
Leu Ser Glu Leu Tyr Tyr Ala Gly Ser His Gly Met Asp Ile Met Ser
            180                 185                 190
Pro Ala Gly Glu Ser Leu Asn His Glu His Ser Arg Thr Val Ser Val
        195                 200                 205
Tyr Glu Gln Gly Lys Asp Val Asn Leu Phe Gln Pro Ala Ser Glu Phe
    210                 215                 220
Leu Pro Met Ile Asp Lys Val Leu Cys Ser Leu Ile Glu Ser Thr Lys
```

```
                225                 230                 235                 240
Asp Ile Lys Gly Val Lys Val Glu Asp Asn Lys Phe Cys Ile Ser Val
                    245                 250                 255

His Tyr Arg Asn Val Glu Glu Lys Asn Trp Thr Leu Val Ala Gln Cys
                260                 265                 270

Val Asp Asp Val Ile Arg Thr Tyr Pro Lys Leu Arg Leu Thr His Gly
            275                 280                 285

Arg Lys Val Leu Glu Ile Arg Pro Val Ile Asp Trp Asp Lys Gly Lys
        290                 295                 300

Ala Val Thr Phe Leu Leu Glu Ser Leu Gly Leu Asn Asn Cys Glu Asp
305                 310                 315                 320

Val Leu Pro Ile Tyr Val Gly Asp Asp Arg Thr Asp Glu Asp Ala Phe
                    325                 330                 335

Lys Val Leu Arg Asp Gly Pro Asn His Gly Tyr Gly Ile Leu Val Ser
                340                 345                 350

Ala Val Pro Lys Asp Ser Asn Ala Phe Tyr Ser Leu Arg Asp Pro Ser
            355                 360                 365

Glu Val Met Glu Phe Leu Lys Ser Leu Val Thr Trp Lys Arg Ser Met
        370                 375                 380

Gly
385

<210> SEQ ID NO 38
<211> LENGTH: 374
<212> TYPE: PRT
<213> ORGANISM: Arabidopsis thaliana

<400> SEQUENCE: 38

Met Thr Asn Gln Asn Val Ile Val Ser Asp Arg Lys Pro Ile Leu Gly
1               5                   10                  15

Leu Lys Thr Ile Thr Val Ser Val Ser Asn Ser Pro Leu Phe Ser Asn
                20                  25                  30

Ser Phe Pro Thr Tyr Phe Asn Phe Pro Arg Arg Lys Leu Leu Lys Leu
            35                  40                  45

Leu Glu Ala Ala Asp Lys Asn Asn Leu Val Val Ala Pro Lys Ile Thr
        50                  55                  60

Ser Met Ile Asp Ser Met Arg Asp Ser Ser Pro Thr Arg Leu Arg Ser
65                  70                  75                  80

Ser Ser Tyr Asp Ser Asp Ser Asp Asn Asp Lys Thr Ser Trp Ile
                85                  90                  95

Val Arg Phe Pro Ser Ala Leu Asn Met Phe Asp Glu Ile Val Asn Ala
                100                 105                 110

Ala Lys Gly Lys Gln Ile Val Met Phe Leu Asp Tyr Asp Gly Thr Leu
            115                 120                 125

Ser Pro Ile Val Glu Asp Pro Asp Lys Ala Phe Ile Thr His Glu Met
        130                 135                 140

Arg Glu Val Val Lys Asp Val Ala Ser Asn Phe Pro Thr Ala Ile Val
145                 150                 155                 160

Thr Gly Arg Ser Ile Glu Lys Val Arg Ser Phe Val Gln Val Asn Glu
                165                 170                 175

Ile Tyr Tyr Ala Gly Ser His Gly Met Asp Ile Glu Gly Pro Thr Asn
            180                 185                 190

Glu Asn Ser Asn Gly Gln Ser Asn Glu Arg Val Leu Phe Gln Pro Ala
        195                 200                 205
```

-continued

```
Arg Glu Phe Leu Pro Met Ile Glu Lys Val Val Asn Ile Leu Glu Glu
    210                 215                 220

Lys Thr Lys Trp Ile Pro Gly Ala Met Val Glu Asn Asn Lys Phe Cys
225                 230                 235                 240

Leu Ser Val His Phe Arg Arg Val Asp Glu Lys Arg Trp Pro Ala Leu
                245                 250                 255

Ala Glu Val Val Lys Ser Val Leu Ile Asp Tyr Pro Lys Leu Lys Leu
                260                 265                 270

Thr Gln Gly Arg Lys Val Leu Glu Ile Arg Pro Thr Ile Lys Trp Asp
            275                 280                 285

Lys Gly Gln Ala Leu Asn Phe Leu Leu Lys Ser Leu Gly Tyr Glu Asn
    290                 295                 300

Ser Asp Val Val Pro Val Tyr Ile Gly Asp Asp Arg Thr Asp Glu
305                 310                 315                 320

Asp Ala Phe Lys Val Leu Arg Glu Arg Gly Gln Gly Phe Gly Ile Leu
                325                 330                 335

Val Ser Lys Val Pro Lys Asp Thr Asn Ala Ser Tyr Ser Leu Gln Asp
                340                 345                 350

Pro Ser Gln Val Asn Lys Phe Leu Glu Arg Leu Val Glu Trp Lys Arg
            355                 360                 365

Lys Thr Val Gly Glu Glu
    370
```

PLANT GENE ENCODING TREHALOSE METABOLISM ENZYMES

This application is a divisional of U.S. application Ser. No. 10/365,970, filed Feb. 13, 2003, now U.S. Pat. No. 7,214,858, issued May 8, 2007, which is a continuation-in-part of U.S. application Ser. No. 09/538,365, filed Mar. 29, 2000, now abandoned, which claims the benefit of U.S. Provisional Application No. 60/127,187, filed Mar. 31, 1999, each of which is herein incorporated by reference in its entirety.

FIELD OF THE INVENTION

This invention is in the field of plant molecular biology. More specifically, this invention pertains to nucleic acid fragments encoding trehalose metabolism enzymes in plants and seeds.

BACKGROUND OF THE INVENTION

Plants encounter a variety of environmental stresses that effect plant water status. The availability of water for nutrient transport, cellular metabolism, evaporative cooling and other biological functions is often impaired by these environmental stresses. One mechanism that all organisms use to tolerate abiotic stress is the accumulation of solutes that do not interfere with normal biochemical reactions. Three of the most effective compatible solutes, as shown by in vitro enzyme stabilization studies are ectoine, hydroxyectoine (unusual methylated cyclic amino acids) and trehalose (Lippert, K. et al. (1992) *Appl. Microbiol. Biotech.* 37:61-65). In fungi, bacteria and invertebrates trehalose plays a major role in desiccation tolerance and several genes have been identified in bacteria that encode enzymes required for trehalose biosynthesis (Bohnert, H. J. et al. (1995) *Plant Cell* 7:1099-1111). Two of the enzymes involved in trehalose biosynthesis are alpha, alpha-trehalose-phosphate synthase, and trehalose-6-phosphate phosphatase. Trehalose is metabolized by the enzyme alpha, alpha-trehalase. Initially, plants were thought to lack the ability to synthesize trehalose and attempts have been made to engineer water-stress tolerance in plants via the expression of microbial genes for trehalose synthesis. However, it has been demonstrated that *Arabidopsis thaliana* possesses a gene for trehalose-6-phosphate synthase, TPS1 (Blazquez et al. (1998) *Plant J* 13:685-689) and at least two genes, AtTPPA and AtTPPB, for trehalose-6-phosphate phosphatase (Vogel, G. et al. (1998) *Plant J* 13(5):673-683). Thus there is a great deal of interest in identifying genes that encode proteins that may be involved in trehalose synthesis in plants. These genes may be used to engineer trehalose synthesis in plants in an effort to produce plants with increased water stress tolerance. Accordingly, the availability of nucleic acid sequences encoding all or a portion of a trehalose-6-phosphate phosphatase, alpha, alpha-trehalase and alpha, alpha-trehalose-phosphate synthase would facilitate studies to better understand or engineer trehalose synthesis in plants and provide genetic tools to produce plants having increased water stress tolerance.

SUMMARY OF THE INVENTION

The present invention concerns isolated polynucleotides comprising (a) a first nucleotide sequence encoding a first polypeptide having alpha, alpha-trehalase activity, wherein the amino acid sequence of the first polypeptide and the amino acid sequence of SEQ ID NOs:2 or 4 have at least 80% sequence identity, (b) a second nucleotide sequence encoding a second polypeptide having alpha, alpha-trehalose-phosphate synthase activity, wherein the amino acid sequence of the second polypeptide and the amino acid sequence of SEQ ID NOs:6, 8, 10, 12 or 14 have at least 80% sequence identity, or (c) a third nucleotide sequence encoding a third polypeptide having trehalose-6-phosphate phosphatase activity, wherein the amino acid sequence of the third polypeptide and the amino acid sequence of SEQ ID NOs:16, 18, 20, 22, or 24 have at least 80% sequence identity. It is preferred that the identity be at least 85%, it is preferable if the identity is at least 90%, it is more preferred that the identity be at least 95%. The present invention also relates to isolated polynucleotides comprising the complement of the nucleotide sequence. More specifically, the present invention concerns isolated polynucleotides encoding the polypeptide sequence of SEQ ID NOs:2, 4, 6, 8, 10, 12, 14, 16, 18, 20, 22, or 24 or nucleotide sequences comprising the nucleotide sequence of SEQ ID NO:1, 3, 5, 7, 9, 11, 13, 15, 17, 19, 21 or 23.

In a first embodiment, the present invention includes an isolated polynucleotide comprising: (a) a first nucleotide sequence encoding a first polypeptide having alpha, alpha-trehalase activity, wherein the first polypeptide has an amino acid sequence of at least 80%, 85%, 90%, or 95% sequence identity, based on the Clustal V method of alignment, when compared to one of SEQ ID NO:2, or 4, (b) a second nucleotide sequence encoding a second polypeptide having alpha, alpha-trehalose-phosphate synthase activity, wherein the second polypeptide has an amino acid sequence of at least 80%, 85%, 90%, or 95% sequence identity, based on the Clustal V method of alignment, when compared to one of SEQ ID NO:6, 8, 10, 12 or 14, (c) a third nucleotide sequence encoding a third polypeptide having trehalose-6-phosphate phosphatase activity, wherein the third polypeptide has an amino acid sequence of at least 80%, 85%, 90%, or 95% sequence identity, based on the Clustal V method of alignment, when compared to one of SEQ ID NO:16, 18, 20, 22, or 24, or (d) a complement of the nucleotide sequence of (a), (b) or (c), wherein the complement and the nucleotide sequence consist of the same number of nucleotides and are 100% complementary. The first polypeptide preferably comprises the amino acid sequence of SEQ ID NOs:2 or 4, the second polypeptide preferably comprises the amino acid sequence of SEQ ID NOs:6, 8, 10, 12 or 14, and the third polypeptide preferably comprises the amino acid sequence of SEQ ID NOs:16, 18, 20, 22 or 24. The first nucleotide sequence preferably comprises the nucleotide sequence of SEQ ID NOs:1 or 3, the second nucleotide sequence preferably comprises the nucleotide sequence of SEQ ID NOs:5, 7, 9, 11 or 13, and the third nucleotide sequence preferably comprises the nucleotide sequence of SEQ ID NOs: 15, 17, 19, 21 or 23.

In a second embodiment, the present invention concerns a recombinant DNA construct comprising any of the isolated polynucleotides of the present invention operably linked to at least one regulatory sequence, and a cell, a plant, and a seed comprising the recombinant DNA construct.

In a third embodiment, the present invention includes a vector comprising any of the isolated polynucleotides of the present invention.

In a fourth embodiment, the present invention concerns a method for transforming a cell comprising transforming a cell with any of the isolated polynucleotides of the present invention. The cell transformed by this method is also included. Advantageously, the cell is eukaryotic, e.g., a yeast or plant cell, or prokaryotic, e.g., a bacterium.

In a fifth embodiment, the present invention includes a method for producing a transgenic plant comprising transforming a plant cell with any of the isolated polynucleotides of the present invention and regenerating a plant from the transformed plant cell. The invention is also directed to the transgenic plant produced by this method, and seed obtained from this transgenic plant.

In a sixth embodiment, the present invention concerns (a) an isolated first polypeptide having alpha, alpha-trehalase activity, wherein the first polypeptide has an amino acid sequence of at least 80%, 85%, 90%, or 95% identity, based on the Clustal V method of alignment, when compared to one of SEQ ID NOs:2 or 4, (b) an isolated second polypeptide having alpha, alpha-trehalose-phosphate synthase activity, wherein the second polypeptide has an amino acid sequence of at least 80%, 85%, 90%, or 95% identity, based on the Clustal V method of alignment, when compared to one of SEQ ID NOs:6, 8, 10, 12 or 14, or (c) an isolated third polypeptide having trehalose-6-phosphate phosphatase activity, wherein the third polypeptide has an amino acid sequence of at least 80%, 85%, 90%, or 95% identity, based on the Clustal V method of alignment, when compared to one of SEQ ID NOs:16, 18, 20, 22 or 14. The first polypeptide preferably comprises one of SEQ ID NOs:2 or 4, the second polypeptide preferably comprises one of SEQ ID NOs:6, 8, 10, 12 or 14, and the third polypeptide preferably comprises one of SEQ ID NOs:16, 18, 20, 22 or 24.

In a seventh embodiment, the present invention includes to a method for isolating a polypeptide having alpha, alpha-trehalase, alpha, alpha-trehalose-phosphate synthase or trehalose-6-phosphate phosphatase activity comprising isolating the polypeptide from a cell or culture medium of the cell, wherein the cell comprises a recombinant DNA construct comprising a polynucleotide of the invention operably linked to at least one regulatory sequence.

In an eighth embodiment, this invention concerns a method for selecting a transformed cell comprising: (a) transforming a host cell with the recombinant DNA construct or an expression cassette of the present invention; and (b) growing the transformed host cell, preferably a plant cell, under conditions that allow expression of the polynucleotide encoding alpha, alpha-trehalase, alpha, alpha-trehalose-phosphate synthase or trehalose-6-phosphate phosphatase in an amount sufficient to complement a null mutant in order to provide a positive selection means.

In a ninth embodiment, this invention concerns a method of altering the level of expression of a alpha, alpha-trehalase, alpha, alpha-trehalose-phosphate synthase or trehalose-6-phosphate phosphatase protein in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the alpha, alpha-trehalase, alpha, alpha-trehalose-phosphate synthase or trehalose-6-phosphate phosphatase protein in the transformed host cell.

A further embodiment of the instant invention is a method for evaluating at least one compound for its ability to inhibit the activity of an alpha, alpha-trehalase, alpha, alpha-trehalose-phosphate synthase or trehalose-6-phosphate phosphatase, the method comprising the steps of: (a) introducing into a host cell a recombinant DNA construct comprising a nucleic acid fragment encoding an alpha, alpha-trehalase, alpha, alpha-trehalose-phosphate synthase or trehalose-6-phosphate phosphatase polypeptide, operably linked to at least one regulatory sequence; (b) growing the host cell under conditions that are suitable for expression of the recombinant DNA construct wherein expression of the recombinant DNA construct results in production of an alpha, alpha-trehalase, alpha, alpha-trehalose-phosphate synthase or trehalose-6-phosphate phosphatase polypeptide in the host cell; (c) optionally purifying the alpha, alpha-trehalase, alpha, alpha-trehalose-phosphate synthase or trehalose-6-phosphate phosphatase polypeptide expressed by recombinant DNA construct in the host cell; (d) treating the alpha, alpha-trehalase, alpha, alpha-trehalose-phosphate synthase or trehalose-6-phosphate phosphatase polypeptide with a compound to be tested; (e) comparing the activity of the alpha, alpha-trehalase, alpha, alpha-trehalose-phosphate synthase or trehalose-6-phosphate phosphatase polypeptide that has been treated with a test compound to the activity of an untreated alpha, alpha-trehalase, alpha, alpha-trehalose-phosphate synthase or trehalose-6-phosphate phosphatase polypeptide, and (f) selecting compounds with potential for inhibitory activity.

BRIEF DESCRIPTION OF THE DRAWING AND SEQUENCE LISTINGS

The invention can be more fully understood from the following detailed description and the accompanying drawing and Sequence Listing which form a part of this application.

FIGS. 1A, 1B and 1C show a sequence alignment of the following: (1) the amino acid sequence of SEQ ID NO:16, the corn trehalose-6-phosphate phosphatase; (2) the amino acid sequence of SEQ ID NO:20, the soybean trehalose-6-phosphate phosphatase; (3) the amino acid sequence of SEQ ID NO:22, a second soybean trehalose-6-phosphate phosphatase; (4) the amino acid sequence of SEQ ID NO:24, a carboxy-terminal portion of the wheat trehalose-6-phosphate phosphatase; (5) the amino acid sequence of an *Arabidopsis thaliana* trehalose-6-phosphate phosphatase, AtTPPA, of Vogel et al. (NCBI GI No. 2944178; SEQ ID NO:37); and (6) the amino acid sequence of a second *Arabidopsis thaliana* trehalose-6-phosphate phosphatase, AtTPPB, of Vogel et al. (NCBI GI No. 2944180; SEQ ID NO:38). A consensus sequence of 397 amino acids was generated and is numbered below these six sequences. The amino acid positions for each sequence is given to the left of each row, and to the right of the final row. An asterisk above an amino acid residue indicates that the position is totally conserved among the given SEQ ID NOs, with respect to the *Arabidopsis thaliana* AtTPPA sequence. Below the sequences are shown two domains, A and B, that are conserved among trehalose-6-phosphate phosphatases, as described in Vogel et al. (1998) *Plant J* 13(5): 673-683. The given sequence for each conserved domain is taken from the *Arabidopsis thaliana* AtTPPA amino acid sequence at these positions.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825.

TABLE 1

Trehalose Metabolism Enzymes

| Protein | Clone Designation | SEQ ID NO: (Nucleotide) | SEQ ID NO: (Amino Acid) |
|---|---|---|---|
| Alpha, Alpha-Trehalase | cs1.pk0105.a2 | 1 | 2 |
| Alpha, Alpha-Trehalase | sdp2c.pk008.n16 (FIS) | 3 | 4 |
| Alpha, Alpha-Trehalose-Phosphate Synthase | p0102.ceraq93r | 5 | 6 |
| Alpha, Alpha-Trehalose-Phosphate Synthase | rls2.pk0002.f4 | 7 | 8 |
| Alpha, Alpha-Trehalose-Phosphate Synthase | rls2.pk0004.b4 | 9 | 10 |
| Alpha, Alpha-Trehalose-Phosphate Synthase | ssm.pk0021.f9 | 11 | 12 |
| Alpha, Alpha-Trehalose-Phosphate Synthase | wlk1.pk0017.e10 (FIS) | 13 | 14 |
| Trehalose-6-Phosphate Phosphatase | p0006.cbyvv20r (FIS) | 15 | 16 |
| Trehalose-6-Phosphate Phosphatase | rls72.pk0035.d8 (FIS) | 17 | 18 |
| Trehalose-6-Phosphate Phosphatase | sls2c.pk002.e16 (FIS) | 19 | 20 |
| Trehalose-6-Phosphate Phosphatase | srn1c.pk002.g19 (FIS) | 21 | 22 |
| Trehalose-6-Phosphate Phosphatase | wre1n.pk187.h5 (FIS) | 23 | 24 |
| Alpha, Alpha-Trehalase | sdp2c.pk008.n16 (EST) | 25 | 26 |
| Alpha, Alpha-Trehalose-Phosphate Synthase | wlk1.pk0017.e10 (EST) | 27 | 28 |
| Trehalose-6-Phosphate Phosphatase | rls72.pk0035.d8 (EST) | 29 | 30 |
| Trehalose-6-Phosphate Phosphatase | sls2c.pk002.e16 (EST) | 31 | 32 |
| Trehalose-6-Phosphate Phosphatase | srn1c.pk002.g19 (EST) | 33 | 34 |
| Trehalose-6-Phosphate Phosphatase | wre1n.pk187.h5 (EST) | 35 | 36 |

SEQ ID NO:37 corresponds to the amino acid sequence of the *Arabidopsis thaliana* trehalose-6-phosphate phosphatase, AtTPPA (NCBI GI No. 2944178).

SEQ ID NO:38 corresponds to the amino acid sequence of the *Arabidopsis thaliana* trehalose-6-phosphate phosphatase, AtTPPB (NCBI GI No. 2944180).

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NO:1, 3, 5, 7, 9, 11, 13, 15, 17, 19, 21 or 23, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises any of the isolated polynucleotides of the present invention operably linked to at least one regulatory sequence.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

The "Clustal V method of alignment" corresponds to the alignment method labeled Clustal V (described by Higgins and Sharp (1989) *CABIOS.* 5:151-153) and found in the Megalign program of the LASERGENE bioinformatics computing suite (DNASTAR Inc., Madison, Wis.). The "default parameters" are the parameters pre-set by the manufacturer of the program and for multiple alignments they correspond to GAP PENALTY=10 and GAP LENGTH PENALTY=10, while for pairwise alignments they are KTUPLE=1, GAP PENALTY=3, WINDOW=5 and DIAGONALS SAVED=5. After alignment of the sequences, using the Clustal V program, it is possible to obtain a "percent identity" by viewing the "sequence distances" table on the same program.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence of SEQ ID NOs: 1, 3, 5, 7, 9, 11, 13, 15, 17, 19, 21 or 23, and the complement of such nucleotide sequences may be used to affect the expression and/or function of an alpha, alpha-trehalase, alpha, alpha-trehalose-phosphate synthase or trehalose-6-phosphate phosphatase in a host cell. A method of using an isolated polynucleotide to affect the level of expression of a polypeptide in a host cell (eukaryotic, such as plant or yeast, prokaryotic such as bacterial) may comprise the steps of: constructing an isolated polynucleotide of the present invention or an isolated recombinant DNA construct of the present invention; introducing the isolated polynucleotide or the isolated recombinant DNA construct into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids.

It is well understood by one skilled in the art that many levels of sequence identity are useful in identifying related polypeptide sequences. Useful examples of percent identities are 50%, 55%, 60%, 65%, 70%, 75%, 80%, 85%, 90%, or 95%, or any integer percentage from 55% to 100%. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403-410; see also the explanation of the BLAST algorithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, recombinant DNA constructs, or chimeric genes. A "transgene" is an isolated nucleic acid fragment or recombinant DNA construct that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence.

When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism. Host organisms containing the transferred nucleic acid fragments are referred to as "transgenic" or "transformed" organisms. Examples of methods of plant transformation include *Agrobacterium*-mediated transformation (De Blaere et al. (1987) *Meth. Enzymol.* 143:277; Ishida Y. et al. (1996) *Nature Biotech.* 14:745-750) and particle-accelerated or "gene gun" transformation technology (Klein et al. (1987) *Nature* (London) 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. The term "transformation" as used herein refers to both stable transformation and transient transformation.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be used by itself or may be used in conjunction with a vector. If a vector is used, the choice of vector is dependent upon the method that will be used to transform host plants as is well known to those skilled in the art.

Standard recombinant DNA and molecular cloning techniques used herein are well known in the art and are described more fully in Sambrook et al. *Molecular Cloning: A Labora-* tory Manual; Cold Spring Harbor Laboratory Press: Cold Spring Harbor, 1989 (hereinafter "Maniatis").

"Motifs" or "subsequences" refer to short regions of conserved sequences of nucleic acids or amino acids that comprise part of a longer sequence. For example, it is expected that such conserved subsequences would be important for function, and could be used to identify new homologues in plants. It is expected that some or all of the elements may be found in a homologue. Also, it is expected that one or two of the conserved amino acids in any given motif may differ in a true homologue.

"PCR" or "polymerase chain reaction" is well known by those skilled in the art as a technique used for the amplification of specific DNA segments (U.S. Pat. Nos. 4,683,195 and 4,800,159).

The present invention concerns isolated polynucleotides comprising (a) a first nucleotide sequence encoding a first polypeptide having alpha, alpha-trehalase activity, wherein the amino acid sequence of the first polypeptide and the amino acid sequence of SEQ ID NOs:2 or 4 have at least 80% sequence identity, (b) a second nucleotide sequence encoding a second polypeptide having alpha, alpha-trehalose-phosphate synthase activity, wherein the amino acid sequence of the second polypeptide and the amino acid sequence of SEQ ID NOs:6, 8, 10, 12 or 14 have at least 80% sequence identity, or (c) a third nucleotide sequence encoding a third polypeptide having trehalose-6-phosphate phosphatase activity, wherein the amino acid sequence of the third polypeptide and the amino acid sequence of SEQ ID NOs:16, 18, 20, 22, or 24 have at least 80% sequence identity. It is preferred that the identity be at least 85%, it is preferable if the identity is at least 90%, it is more preferred that the identity be at least 95%.

This invention also includes to the isolated complement of such polynucleotides, wherein the complement and the polynucleotide consist of the same number of nucleotides, and the nucleotide sequences of the complement and the polynucleotide have 100% complementarity.

Nucleic acid fragments encoding at least a portion of several alpha, alpha-trehalase, alpha, alpha-trehalose-phosphate synthase or trehalose-6-phosphate phosphatase have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other alpha, alpha-trehalase, alpha, alpha-trehalose-phosphate synthase or trehalose-6-phosphate phosphatase, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Nat. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence of SEQ ID NOs: 1, 3, 5, 7, 9, 11, 13, 15, 17, 19, 21 or 23, and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention concerns viruses and host cells comprising either the recombinant DNA constructs of the invention as described herein or isolated polynucleotides of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of trehalose in those cells.

Overexpression of the polypeptides of the instant invention may be accomplished by first constructing a recombinant DNA construct in which the coding region is operably linked to a promoter capable of directing expression of a polypeptide in the desired tissues at the desired stage of development. The recombinant DNA construct may comprise promoter sequences and translation leader sequences derived from the same genes. 3' Non-coding sequences corresponding to transcription termination signals may also be provided. The instant recombinant DNA construct may also comprise one or more introns in order to facilitate expression of the recombinant DNA construct.

Plasmid vectors comprising the instant isolated polynucleotide(s) (or recombinant DNA construct(s)) may be constructed. The choice of plasmid vector is dependent upon the method that will be used to transform host plants. The skilled artisan is well aware of the genetic elements that must be present on the plasmid vector in order to successfully transform, select and propagate host cells containing the recombinant DNA construct or chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the recombinant DNA construct(s) described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100: 1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns (a) an isolated first polypeptide having alpha, alpha-trehalase activity, wherein the first polypeptide has an amino acid sequence of at least 80%, 85%, 90%, or 95% identity, based on the Clustal V method of alignment, when compared to one of SEQ ID NOs:2 or 4, (b) an isolated second polypeptide having alpha, alpha-trehalose-phosphate synthase activity, wherein the second polypeptide has an amino acid sequence of at least 80%, 85%, 90%, or 95% identity, based on the Clustal V method of alignment, when compared to one of SEQ ID NOs:6, 8, 10, 12 or 14, or (c) an isolated third polypeptide having trehalose-6-phosphate phosphatase activity, wherein the third polypeptide has an amino acid sequence of at least 80%, 85%, 90%, or 95% identity, based on the Clustal V method of alignment, when compared to one of SEQ ID NOs:16, 18, 20, 22 or 14.

The instant polypeptides (or portions thereof may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA construct for production of the instant polypeptides. This recombinant DNA construct could then be introduced into appropriate microorganisms via transformation to provide high level expression of the encoded alpha, alpha-trehalase, alpha, alpha-trehalose-phosphate synthase or trehalose-6-phosphate phosphatase. An example of a vector for high level expression of the instant polypeptides in a bacterial host is provided (Example 8).

Additionally, the instant polypeptides can be used as a target to facilitate design and/or identification of inhibitors of those enzymes that may be useful as herbicides. This is desirable because the polypeptides described herein catalyze various steps in trehalose metabolism. Accordingly, inhibition of the activity of one or more of the enzymes described herein could lead to inhibition of plant growth. Thus, the instant polypeptides could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as Map-Maker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

Nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several kb to several hundred kb; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci. USA* 86:9402-9406; Koes et al. (1995) *Proc. Natl. Acad. Sci. USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptide disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries

Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cs1 | Corn leaf, sheath 5 wk plant | cs1.pk0105.a2 |
| p0006 | Corn young shoot | p0006.cbyvv20r |
| p0102 | Corn early meiosis tassels, 16-18 cm long* | p0102.ceraq93r |
| rls2 | Rice leaf (15 days after gremination) 2 hrs after infection of *Magnaporta grisea* strain 4360-R-62 (AVR2-YAMO) | rls2.pk0002.f4 rls2.pk0004.b4 |
| rls72 | Rice leaf (15 days after germination) 72 hours after infection of *Magnaporta grisea* strain 4360-R-67 (avr2-yamo) | rls72.pk0035.d8 |
| sdp2c | Soybean developing pods 6-7 mm | sdp2c.pk008.n16 |

TABLE 2-continued cDNA Libraries from Corn, Rice, Soybean and Wheat

| Library | Tissue | Clone |
|---------|--------|-------|
| sls2c | Soybean infected with *Sclerotinia sclerotiorum* mycelium. | sls2c.pk002.e16 |
| srn1c | Soybean developing root nodules. | srn1c.pk002.g19 |
| ssm | Soybean shoot meristem | ssm.pk0021.f9 |
| wlk1 | Wheat seedlings 1 hr after treatment with herbicide** | wlk1.pk0017.e10 |
| wre1n | Wheat root; 7 day old etiolated seedling* | wre1n.pk187.h5 |

*These libraries were normalized essentially as described in U.S. Pat. No. 5,482,845, incorporated herein by reference.

**Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phred/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding trehalose metabolism enzymes were identified by conducting BLAST (Basic Local Alignment Search Tool; Altschul et al. (1993) *J. Mol. Biol.* 215: 403-410; see also the explanation of the BLAST alogarithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389-3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Alpha, Alpha-Trehalase

The BLASTX search using the EST sequences from clones listed in Table 3 revealed similarity of the polypeptides encoded by the cDNAs alpha, alpha-trehalase from *Glycine max* (NCBI General Identifier No. gi 4559292) and *Neurospora crassa* (NCBI General Identifier No. gi 3929389). Shown in Table 3 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 3

BLAST Results for Sequences Encoding Polypeptides Homologous to *Glycine max* and *Neurospora crassa* Alpha, Alpha-Trehalase

| Clone | Status | BLAST pLog Score to |
|---|---|---|
| cs1.pk0105.a2 | FIS | 133.00 (gi 4559292) |
| sdp2c.pk008.n16 | FIS | 69.70 (gi 3929389) |

The data in Table 4 represents a calculation of the percent identity of the amino acid sequences set forth in SEQ ID NOs:2 and 4 and the *Glycine max* and *Neurospora crassa* sequences.

TABLE 4

Percent Identity of Amino Acid Sequences Deduced From the Nucleotide Sequences of cDNA Clones Encoding Polypeptides Homologous to *Glycine max* and *Neurospora crassa* Alpha, Alpha-Trehalase

| SEQ ID NO. | Percent Identity to |
|---|---|
| 2 | 59% (gi 4559292) |
| 4 | 35% (gi 3929389) |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of an alpha, alpha-trehalase. These sequences represent the first corn sequence and a new soybean sequence encoding alpha, alpha-trehalase, known to the Applicant.

Example 4

Characterization of cDNA Clones Encoding Alpha, Alpha-Trehalose-Phosphate Synthase The BLASTX search using the EST sequences from clones listed in Table 5 revealed similarity of the polypeptides encoded by the cDNAs alpha, alpha-trehalose-phosphate synthase from *Arabidopsis thaliana* (NCBI GI No. 6553894) and *Schizosaccharomyces pombe* (NCBI GI No. 730984). Shown in Table 5 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 5

BLAST Results for Sequences Encoding Polypeptides Homologous *Arabidopsis thaliana* and *Schizosaccharomyces pombe* Alpha, Alpha-Trehalose-Phosphate Synthase

| Clone | Status | BLAST pLog Score |
|---|---|---|
| p0102.ceraq93r | EST | 97.50 (gi 6553894) |
| rls2.pk0002.f4 | FIS | >254.00 (gi 6553894) |
| rls2.pk0004.b4 | FIS | >254.00 (gi 6553894) |
| ssm.pk0021.f9 | FIS | >254.00 (gi 6553894) |
| wlk1.pk0017.e10 | EST | 67.52 (gi 730984) |

The data in Table 6 represents a calculation of the percent identity of the amino acid sequences set forth in SEQ ID NOs:6, 8, 10, 12 and 14 and the *Arabidopsis thaliana* and *Schizosaccharomyces pombe* sequences.

TABLE 6

Percent Identity of Amino Acid Sequences Deduced From the
Nucleotide Sequences of cDNA Clones Encoding Polypeptides
Homologous to *Arabidopsis thaliana* and *Schizosaccharomyces pombe*
Alpha, Alpha-Trehalose-Phosphate Synthase

| SEQ ID NO. | Percent Identity to |
|---|---|
| 6 | 63% (gi 6553894) |
| 8 | 59% (gi 6553894) |
| 10 | 57% (gi 6553894) |
| 12 | 64% (gi 6553894) |
| 14 | 33% (gi 730984) |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10. Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of an alpha, alpha-trehalose-phosphate synthase. These sequences represent the first corn, rice, soybean and wheat sequences encoding alpha, alpha-trehalose-phosphate synthase known to the Applicant.

Example 5

Characterization of cDNA Clones Encoding Trehalose-6-Phosphate Phosphatase

The BLASTX search using the EST sequences from clones listed in Table 7 revealed similarity of the polypeptides encoded by the cDNAs trehalose-6-phosphate phosphatase from *Arabidopsis thaliana* (NCBI GI No. 6587856), *Arabidopsis thaliana* (NCBI GI No. 2944178; AtTPPA) and *Arabidopsis thaliana* (NCBI GI No. 2944180; AtTPPB). Shown in Table 7 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 7

BLAST Results for Sequences Encoding Polypeptides Homologous
to *Arabidopsis thaliana* Trehalose-6-Phosphate Phosphatase

| Clone | Status | BLAST pLog Score |
|---|---|---|
| p0006.cbyvv20r | CGS | 112.00 (gi 2944178) |
| rls72.pk0035.d8 | FIS | 55.00 (gi 6587856) |
| sls2c.pk002.e16 | CGS | 134.00 (gi 2944178) |
| srn1c.pk002.g19 | FIS | 120.00 (gi 2944180) |
| wre1n.pk187.h5 | FIS | 82.52 (gi 2944178) |

FIGS. 1A-1C show a sequence alignment of the amino acid sequences for the trehalose-6-phosphate phosphatases from corn (SEQ ID NO:16), soybean (SEQ ID NOs:20 and 22), wheat (SEQ ID NO:24) and *Arabidopsis thaliana* (AtTPPA, SEQ ID NO:37, and AtTPPB, SEQ ID NO:38). The amino acid sequence of the second soybean trehalose-6-phosphate phosphatase (SEQ ID NO:22) is almost full-length, missing approximately ten to twenty amino acids at the amino-terminus, as compared to the other soybean trehalose-6-phosphate phosphatase (SEQ ID NO:20). The amino acid sequence of the wheat trehalose-6-phosphate phosphatase (SEQ ID NO:24) corresponds to the carboxy-terminal 226 amino acids of the protein. An asterisk above an amino acid residue indicates that the position is totally conserved among the given SEQ ID NOs, with respect to the *Arabidopsis thaliana* AtTPPA sequence. Below the sequences are shown two domains, A and B, that are conserved among trehalose-6-phosphate phosphatases, as described in Vogel et al. (1998) *Plant J* 13(5):673-683. The given sequence for each conserved domain is taken from the *Arabidopsis thaliana* AtTPPA amino acid sequence at these positions. FIGS. 1A-1C indicate that regions of high sequence similarity are located in the carboxy-terminal 70% of the consensus sequence. Vogel et al. have noted that the AtTPPA and AtTPPB proteins have high sequence conservation to each other except for the amino-terminal 100 amino acids, which they note have features in common with chloroplast transit peptides. Vogel et al. have shown enzyme activity for AtTPPA, AtTPPB, and a truncated AtTPPA polypeptide that is missing the first 91 amino acids.

The data in Table 8 represents a calculation of the percent identity of the amino acid sequences set forth in SEQ ID NOs:16, 18, 20, 22 and 24 and the *Arabidopsis thaliana* sequences for AtTPPA (GI No. 2944178; SEQ ID NO:37), AtTPPB (GI No. 2944180; SEQ ID NO:38) and a variant of AtTPPB (GI No. 6587856).

TABLE 8

Percent Identity of Amino Acid Sequences Deduced From the
Nucleotide Sequences of cDNA Clones Encoding Polypeptides
Homologous to Trehalose-6-Phosphate Phosphatase

| SEQ ID NO. | Percent Identity to |
|---|---|
| 16 (corn) | 55% (gi 2944178; AtTPPA) |
| 18 (rice) | 54% (gi 6587856; AtTPPB) |
| 20 (soy) | 60% (gi 2944178; AtTPPA) |
| 22 (soy) | 59% (gi 2944180; AtTPPB) |
| 24 (wheat) | 64% (gi 2944178; AtTPPA) |

The data in Table 9 shows the percent identity for each pair of amino acid sequences from SEQ ID NOs:16, 18, 20, 22, 24, 37, 38 and an enzymatically active fragment of SEQ ID NO:37 in which the first 91 amino acids are missing (Vogel et al. (1998) *Plant J* 13(5):673-683).

TABLE 9

Percent Sequence Identity of Amino Acid Sequences of Plant
Trehalose-6-Phosphate Phosphatases With Each Other

| SEQ ID NO: | Percent Identity to SEQ ID NO: | | | | | | | |
|---|---|---|---|---|---|---|---|---|
| | 16 | 18 | 20 | 22 | 24 | 37 | 37t* | 38 |
| 16 | — | 56% | 54% | 49% | 82% | 55% | 61% | 48% |
| 18 | 56% | — | 49% | 59% | 51% | 51% | 51% | 54% |
| 20 | 54% | 49% | — | 47% | 63% | 60% | 66% | 46% |
| 22 | 49% | 59% | 47% | — | 58% | 47% | 55% | 59% |
| 24 | 82% | 51% | 63% | 58% | — | 64% | 64% | 57% |
| 37 | 55% | 51% | 60% | 47% | 64% | — | 100% | 47% |
| 37t* | 61% | 51% | 66% | 55% | 64% | 100% | — | 55% |
| 38 | 48% | 54% | 46% | 59% | 57% | 47% | 55% | — |

*37t refers to the truncated AtTPPA polypeptide that is missing 91 amino acids from the amino terminus.

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a trehalose-6-phosphate phosphatase. These sequences represent the first corn, rice, soybean and wheat sequences encoding trehalose-6-phosphate phosphatase that are known to the Applicant.

Example 6

Expression of Recombinant DNA Constructs in Monocot Cells

A recombinant DNA construct comprising a cDNA encoding one of the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding one of the instant polypeptides, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 7

Expression of Recombinant DNA Constructs in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding one of the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL CaCl₂ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 8

Expression of Recombinant DNA Constructs in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and Hind III sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 µL of water. Appropriate oligonucleotide adapters may be ligated to the fragment using T4 DNA ligase (New England Biolabs (NEB), Beverly, Mass.).

The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight. Alpha, alpha-trehalase activity can be determined by the method of Kalf and Rieder (1958) *J Biol Chem* 230:691-698. Alpha, alpha-trehalose-phosphate synthase activity can be determined by the method of Blazquez et al. (1998) *Plant J* 13:685-689. Trehalose-6-phosphate phosphatase activity can be determined by the method of Vogel, G. et al. (1998) *Plant J* 13(5):673-683.

Example 9

Expression of Recombinant DNA Constructs in Yeast Cells

The polypeptides encoded by the polynucleotides of the instant invention may be expressed in a yeast (*Saccharomyces cerevisiae*) strain YPH. Plasmid DNA may be used as template to amplify the portion encoding the alpha, alpha-trehalase, alpha, alpha-trehalose-phosphate synthase or trehalose-6-phosphate phosphatase. Amplification may be performed using the GC melt kit (Clontech) with a 1 M final concentration of GC melt reagent and using a Perkin Elmer 9700 thermocycler. The amplified insert may then be incubated with a modified pRS315 plasmid (NCBI General Identifier No. 984798; Sikorski, R. S, and Hieter, P. (1989) *Genetics* 122:19-27) that has been digested with Not I and Spe I. Plasmid pRS315 has been previously modified by the insertion of a bidirectional gal1/10 promoter between the Xho I and Hind III sites. The plasmid may then be transformed into the YPH yeast strain using standard procedures where the insert recombines through gap repair to form the desired transformed yeast strain (Hua, S. B. et al. (1997) *Plasmid* 38:91-96).

Yeast cells may be prepared according to a modification of the methods of Pompon et al. (Pompon, D. et al. (1996) *Meth. Enz.* 272:51-64). Briefly, a yeast colony will be grown overnight (to saturation) in SG (-Leucine) medium at 30° C. with good aeration. A 1:50 dilution of this culture will be made into 500 mL of YPGE medium with adenine supplementation and allowed to grow at 30° C. with good aeration to an $OD_{600}$ of 1.6 (24-30 h). Fifty mL of 20% galactose will be added, and the culture allowed to grow overnight at 30° C. The cells will be recovered by centrifugation at 5,500 rpm for five minutes in a Sorvall GS-3 rotor. The cell pellet resuspended in 500 mL of 0.1 M potassium phosphate buffer (pH 7.0) and then allowed to grow at 30° C. for another 24 hours.

The cells may be recovered by centrifugation as described above and the presence of the polypeptide of the instant invention determined by HPLC/mass spectrometry or any other suitable method.

Example 10

Expression of Recombinant DNA Constructs in Insect Cells

The cDNAs encoding the instant polypeptides may be introduced into the baculovirus genome itself. For this purpose the cDNAs may be placed under the control of the polyhedron promoter, the IE1 promoter, or any other one of the baculovirus promoters. The cDNA, together with appropriate leader sequences is then inserted into a baculovirus transfer vector using standard molecular cloning techniques. Following transformation of *E. coli* DH5α, isolated colonies are chosen and plasmid DNA is prepared and is analyzed by restriction enzyme analysis. Colonies containing the appropriate fragment are isolated, propagated, and plasmid DNA is prepared for cotransfection.

*Spodoptera frugiperda* cells (Sf-9) are propagated in ExCell® 401 media (JRH Biosciences, Lenexa, Kans.) supplemented with 3.0% fetal bovine serum. Lipofectin® (50 μL at 0.1 mg/mL, Gibco/BRL) is added to a 50 μL aliquot of the transfer vector containing the toxin gene (500 ng) and linearized polyhedrin-negative AcNPV (2.5 μg, Baculogold®) viral DNA, Pharmigen, San Diego, Calif.). Sf-9 cells (approximate 50% monolayer) are co-transfected with the viral DNA/transfer vector solution. The supernatant fluid from the co-transfection experiment is collected at 5 days post-transfection and recombinant viruses are isolated employing standard plaque purification protocols, wherein only polyhedrin-positive plaques are selected (O'Reilly et al. (1992), *Baculovirus Expression Vectors: A Laboratory Manual*, W. H. Freeman and Company, New York.). Sf-9 cells in 35 mM petri dishes (50% monolayer) are inoculated with 100 μL of a serial dilution of the viral suspension, and supernatant fluids are collected at 5 days post infection. In order to prepare larger quantities of virus for characterization, these supernatant fluids are used to inoculate larger tissue cultures for large-scale propagation of recombinant viruses. Expression of the instant polypeptides encoded by the recombinant baculovirus is confirmed by any of the methods mentioned in Example 8.

What is claimed is:

1. An isolated polynucleotide comprising:
   (a) a nucleotide sequence encoding a polypeptide having trehalose-6-phosphate phosphatase activity, wherein the polypeptide has an amino acid sequence of at least 95% sequence identity, when compared to SEQ ID NO:20, or
   (b) the complement of the nucleotide sequence of (a), wherein the complement and the nucleotide sequence consist of the same number of nucleotides and are 100% complementary.

2. The polynucleotide of claim 1, wherein the amino acid sequence of the polypeptide comprises SEQ ID NO:20.

3. The polynucleotide of claim 1, wherein the nucleotide sequence comprises SEQ ID NO:19.

4. A vector comprising the polynucleotide of claim 1.

5. A recombinant DNA construct comprising the polynucleotide of claim 1 operably linked to at least one regulatory sequence.

6. A method for transforming a cell, wherein the method comprises transforming a cell with the polynucleotide of claim 1.

7. A cell comprising the recombinant DNA construct of claim 5.

8. A method for producing a plant, wherein the method comprises transforming a plant cell with the polynucleotide of claim 1 and regenerating a plant from the transformed plant cell.

9. A plant comprising the recombinant DNA construct of claim 5.

10. A seed comprising the recombinant DNA construct of claim 5.

11. A method for isolating a polypeptide having trehalose-6-phosphate phosphatase activity, wherein the method comprises isolating the polypeptide from a cell or culture medium of the cell, wherein the cell comprises a recombinant DNA construct comprising the polynucleotide of claim 1 operably linked to at least one regulatory sequence.

12. A method of altering the level of expression of a trehalose-6-phosphate phosphatase in a host cell, wherein the method comprises:
   (a) transforming a host cell with the recombinant DNA construct of claim 5; and
   (b) growing the transformed host cell under conditions that are suitable for expression of the recombinant DNA construct wherein expression of the recombinant DNA construct results in production of altered levels of the trehalose-6-phosphate phosphatase in the transformed host cell.

* * * * *